(12) United States Patent
Cendrillon et al.

(10) Patent No.: US 11,963,748 B2
(45) Date of Patent: *Apr. 23, 2024

(54) PORTABLE MONITOR FOR HEART RATE DETECTION

(71) Applicant: Verily Life Sciences LLC, Mountain View, CA (US)

(72) Inventors: Raphael Cendrillon, Mountain View, CA (US); Ali Shoeb, Mill Valley, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/886,299

(22) Filed: Aug. 11, 2022

(65) Prior Publication Data

US 2023/0033353 A1 Feb. 2, 2023

Related U.S. Application Data

(63) Continuation of application No. 15/673,585, filed on Aug. 10, 2017, now Pat. No. 11,419,509.

(Continued)

(51) Int. Cl.
*A61B 5/024* (2006.01)
*A61B 5/00* (2006.01)
(Continued)

(52) U.S. Cl.
CPC ........ *A61B 5/02416* (2013.01); *A61B 5/0002* (2013.01); *A61B 5/02438* (2013.01);
(Continued)

(58) Field of Classification Search
CPC .............. A61B 5/02416; A61B 5/0002; A61B 5/02438; A61B 5/0533; A61B 5/1112;
(Continued)

(56) References Cited

U.S. PATENT DOCUMENTS 5,749,366 A 5/1998 Odagiri et al.
9,107,644 B2 8/2015 Frix et al.
(Continued)

OTHER PUBLICATIONS

USPTO Office Action dated Mar. 19, 2019, in corresponding U.S. Appl. No. 15/673,585, 19 pages.
(Continued)

*Primary Examiner* — Carl H Layno
*Assistant Examiner* — Michael J Lau
(74) *Attorney, Agent, or Firm* — CHRISTENSEN O'CONNOR JOHNSON KINDNESS PLLC

(57) ABSTRACT

The present invention is directed to a wearable fitness and/or heart rate monitoring device which includes motion detecting sensor(s), a galvanic skin response (GSR) sensor, a user input interface, or any combination thereof. The device accounts for signal noise, produced when an individual passes thru varying exercise states, by filtering out the motion of the individual using a 3-axis accelerometer. The invention also provides for systems and methods of operating the monitor which extracts and/or stores true or correct heart rate values from the heartbeat waveform signal observed from a PPG.

17 Claims, 10 Drawing Sheets

Related U.S. Application Data

(60) Provisional application No. 62/376,678, filed on Aug. 18, 2016.

(51) Int. Cl.
    *A61B 5/0533*     (2021.01)
    *A61B 5/11*       (2006.01)

(52) U.S. Cl.
     CPC .......... *A61B 5/0533* (2013.01); *A61B 5/1112* (2013.01); *A61B 5/1118* (2013.01); *A61B 5/725* (2013.01); *A61B 2562/0219* (2013.01)

(58) Field of Classification Search
     CPC ................. A61B 5/1118; A61B 5/725; A61B 2562/0219
     USPC ........................................................ 600/301
     See application file for complete search history.

(56) References Cited

U.S. PATENT DOCUMENTS

| | | |
|---|---|---|
| 9,339,236 B2 | 5/2016 | Frix et al. |
| 9,339,237 B2 | 5/2016 | Frix et al. |
| 2005/0124463 A1 | 6/2005 | Yeo et al. |
| 2005/0228298 A1 | 10/2005 | Banet et al. |
| 2007/0161874 A1 | 7/2007 | Aerts |
| 2009/0043216 A1 | 2/2009 | Lin et al. |
| 2010/0113893 A1 | 5/2010 | Cohen et al. |
| 2010/0298656 A1 | 11/2010 | McCombie et al. |
| 2011/0275910 A1* | 11/2011 | Amos ................ A61B 5/02416 600/301 |
| 2011/0300847 A1 | 12/2011 | Quy |
| 2012/0053433 A1 | 3/2012 | Chamoun et al. |
| 2012/0083705 A1 | 4/2012 | Yuen et al. |
| 2012/0150052 A1* | 6/2012 | Buchheim .............. A61B 5/721 600/500 |
| 2012/0310100 A1 | 12/2012 | Galen et al. |
| 2013/0171599 A1 | 7/2013 | Bleich et al. |
| 2014/0128753 A1 | 5/2014 | Luna et al. |
| 2014/0128754 A1 | 5/2014 | Luna et al. |
| 2014/0213862 A1 | 7/2014 | Addison et al. |
| 2014/0248835 A1* | 9/2014 | Lee ...................... H04W 88/04 455/7 |
| 2014/0275854 A1* | 9/2014 | Venkatraman ....... A61B 5/1123 600/479 |
| 2014/0278139 A1 | 9/2014 | Hong et al. |
| 2014/0288435 A1* | 9/2014 | Richards .............. A61B 5/1123 600/479 |
| 2015/0038840 A1 | 2/2015 | Hassan et al. |
| 2015/0065889 A1* | 3/2015 | Gandelman ........ A61B 5/02438 600/479 |
| 2015/0112606 A1 | 4/2015 | He et al. |
| 2015/0250418 A1 | 9/2015 | Ashby |
| 2015/0251074 A1 | 9/2015 | Ahmed et al. |
| 2015/0265170 A1 | 9/2015 | Wisloff et al. |
| 2015/0272457 A1 | 10/2015 | Etemad et al. |
| 2016/0007935 A1 | 1/2016 | Hernandez et al. |
| 2016/0022220 A1* | 1/2016 | Lee .................... A61B 5/02433 600/479 |
| 2016/0038037 A1 | 2/2016 | Kovacs |
| 2016/0051201 A1* | 2/2016 | Maani .................. A61B 5/7278 600/301 |
| 2016/0058367 A1 | 3/2016 | Raghuram et al. |
| 2016/0081627 A1 | 3/2016 | McGloin et al. |
| 2016/0089038 A1 | 3/2016 | Chadderdon, III et al. |
| 2016/0094899 A1 | 3/2016 | Aumer et al. |
| 2016/0120434 A1 | 5/2016 | Park et al. |
| 2016/0150978 A1* | 6/2016 | Yuen .................... A61B 5/0205 600/301 |
| 2016/0151013 A1 | 6/2016 | Atallah et al. |
| 2016/0196635 A1* | 7/2016 | Cho ......................... G06T 3/40 345/660 |
| 2016/0198996 A1 | 7/2016 | Dullen |

OTHER PUBLICATIONS

USPTO Office Action dated Sep. 10, 2019, in corresponding U.S. Appl. No. 15/673,585, 19 pages.
USPTO Office Action dated May 11, 2020, in corresponding U.S. Appl. No. 15/673,585, 15 pages.
USPTO Office Action dated Sep. 9, 2020, in corresponding U.S. Appl. No. 15/673,585, 16 pages.
USPTO Office Action dated Mar. 11, 2021, in corresponding U.S. Appl. No. 15/673,585, 19 pages.
USPTO Office Action dated Nov. 12, 2021, in corresponding U.S. Appl. No. 15/673,585, 17 pages.
USPTO Notice of Allowance dated Apr. 4, 2022, in corresponding U.S. Appl. No. 15/673,585, 16 pages.

* cited by examiner

| ACTIVITY | NO PRIOR (MAE BPM) | MOTION PRIOR (MAE BPM) |
|---|---|---|
| INDOOR SIT | 6.8 | 8.3 |
| INDOOR WALK | 7.3 | 8.3 |
| INDOOR JOG | 11.8 | 9.0 |
| INDOOR RUN | 10.8 | 4.4 |
| OUTDOOR SIT | 9.4 | 5.1 |
| OUTDOOR WALK | 18.1 | 13.1 |
| OUTDOOR RUN | 14.3 | 10.8 |

FIG. 9

PORTABLE MONITOR FOR HEART RATE DETECTION

CROSS-REFERENCE TO RELATED APPLICATION

This application is a continuation of U.S. Non-Provisional patent application Ser. No. 15/673,585, filed Aug. 10, 2017, now U.S. Pat. No. 11,419,509, which claims the benefit of U.S. Provisional Pat. App. No. 62/376,678, filed Aug. 18, 2016, the contents both of which are hereby incorporated by reference.

BACKGROUND

Interest in the personal health consumer space has led to a variety of health tracking devices being developed. Modern electronic engineering has developed small-sized personal health monitoring devices known as "biometric tracking" or "biometric monitoring" devices. These devices are popular not only for the exercise or health data they provide a user, but also for their portability. Devices like these often include a display, battery, and a plurality of very small sensors all residing inside a small housing. Such devices may be used to determine a host of parameters reflective of a wearer's personal health and/or exercise.

Continuous human pulse rate estimation from a wearable device can be valuable in effecting accurate health monitoring devices and reporting fitness-related exercise values of an individual. Continuous pulse rate estimation in wearable devices may be negatively affected by the wide dynamic range of pulse rates under different physiologic and activity states. Human pulse rate varies greatly, for instance, during the sleep state when compared to an exercising state. Moreover, pulse rate can vary significantly within individual physiological states such as when a subject is exercising.

There are many wearable devices for tracking heart rate. These devices may estimate human pulse rate from a variety of incoming signals which may contain a plurality of heart rate values.

SUMMARY

Some embodiments of the present disclosure provide a wearable device that includes: (i) a photoplethysmographic sensor; (ii) a motion sensor; (iii) a communication interface; and (iv) a controller that is operably coupled to the photoplethysmographic sensor, the motion sensor, and the communication interface. The controller is configured to perform operations including: (a) detecting, using the photoplethysmographic sensor, a photoplethysmographic signal related to cardiovascular activity of a user; (b) detecting, using the motion sensor, a motion signal related to motion of the user; (c) generating, using the motion signal, a motion-compensated cardiovascular signal based on the photoplethysmographic signal; (d) transmitting, using the communication interface, an indication of the motion signal to a remote system; and (e) transmitting, using the communication interface, an indication of the motion-compensated cardiovascular signal to the remote system.

In some embodiments, the operations performed by the controller further include determining an activity state of the user. Determining the activity state of the user can include determining the activity state based on the motion signal. In such embodiments, transmitting an indication of the motion signal to the remote system can include transmitting an indication of the determined activity state.

In some embodiments, the wearable device may further include a galvanic skin response sensor. In such embodiments, the controller operations may further include detecting, using the galvanic skin response sensor, a galvanic skin response signal related to a galvanic skin response of the user. In such embodiments, determining the activity state of the user could further include determining the activity state based on the galvanic skin response signal.

In some embodiments, the motion sensor includes a global positioning system receiver.

In some embodiments, detecting the motion signal can include using the motion sensor to generate a plurality of motion signals. In such examples, generating a motion-compensated cardiovascular signal based on the photoplethysmographic signal can include generating a plurality of filtered motion signals and subtracting each of the filtered acceleration signals from the photoplethysmographic signal. Generating a particular filtered motion signal of the plurality of filtered motion signals can include using a finite impulse response filter to generate the particular filtered motion signal based on a respective motion signal of the plurality of motion signals.

In some embodiments, the motion sensor includes a 3-axis accelerometer. In such embodiments, detecting a motion signal related to motion of the user may include generating first, second, and third acceleration signals using the 3-axis accelerometer. In such embodiments, generating a motion-compensated cardiovascular signal based on the photoplethysmographic signal may include: (i) generating, using a first finite impulse response filter, a first filtered acceleration signal based on the first acceleration signal; (ii) generating, using a second finite impulse response filter, a second filtered acceleration signal based on the second acceleration signal; (iii) generating, using a third finite impulse response filter, a third filtered acceleration signal based on the third acceleration signal; and (iv) subtracting the first, second, and third filtered acceleration signals from the photoplethysmographic signal.

In some embodiments, the wearable device may further include a memory. In such embodiments, the controller operations may further include: (i) storing, in the memory, a first record of the motion-compensated cardiovascular signal, and (ii) storing, in the memory, a second record of the motion signal. In such embodiments, transmitting an indication of the motion-compensated cardiovascular signal to the remote system may include transmitting an indication of the first record and transmitting an indication of the motion signal to the remote system may include transmitting an indication of the second record.

In some embodiments, the controller operations may further include: (i) determining spectral contents of the motion-compensated cardiovascular signal; and (ii) detecting at least one peak associated with a frequency range or frequency value in the determined spectral contents. In such embodiments, transmitting an indication of the motion-compensated cardiovascular signal to the remote system may include transmitting an indication of the detected at least one peak. In such embodiments, the photoplethysmographic sensor may include a light emitter and a photodetector and the wearable device may further include a digital to analog converter and an analog to digital converter. In such embodiments, the controller operations may further include: (i) generating, using the analog to digital converter during a first period of time, a first sample of an output of the photodetector; and (ii) determining an ambient light offset voltage based on the first sample. In such embodiments, detecting a photoplethysmographic signal related to cardiovascular activity of a user may include: (a) illuminating, using the light emitter during a second period of time, skin of the user; (b) generating, using the digital to analog converter during the second period of time, an offset voltage based on the determined ambient offset voltage; and (c) generating, using the analog to digital converter during the second period of time, a second sample of a difference between the output of the photodetector and the offset voltage generated by the digital to analog converter.

In some embodiments, the wearable device may further include a display. In such examples, the controller operation could further include: (i) receiving, using the communication interface, an indication of a heart rate from the remote system, and (ii) operating the display to provide an indication of the heart rate.

Some embodiments of the present disclosure provide a method that includes: (i) detecting, using a photoplethysmographic sensor of a wearable device, a photoplethysmographic signal (that may be related to cardiovascular activity of a user); (ii) detecting, using a motion sensor of the wearable device, a motion signal (that may be related to motion of the user); (iii) generating, using the motion signal, a motion-compensated cardiovascular signal based on the photoplethysmographic signal; (iv) transmitting an indication of the motion signal to a remote system; (v) transmitting an indication of the motion-compensated cardiovascular signal to the remote system; (iv) receiving an indication of a heart rate from the remote system; and (vi) operating a display of the wearable device to provide an indication of the heart rate.

In some embodiments, the method may further include determining an activity state (e.g., of a user or wearer of the device). Determining the activity state may include determining the activity state based on the motion signal. In such embodiments, transmitting an indication of the motion signal to the remote system may include transmitting an indication of the determined activity state.

In some embodiments, the method may further include detecting, using a galvanic skin response sensor of the wearable device, a galvanic skin response signal (e.g., that is related to a galvanic skin response of a user or wearer of the device). In such embodiments, determining the activity state may further include determining the activity state based on the galvanic skin response signal.

In some embodiments, generating, using the motion signal, the motion-compensated cardiovascular signal based on the photoplethysmographic signal is performed by the remote system. Additionally or alternatively, generating, using the motion signal, a motion-compensated cardiovascular signal based on the photoplethysmographic signal may be performed by a controller of the wearable device.

In some embodiments, detecting a motion signal may include generating first, second, and third acceleration signals. In such embodiments, generating a motion-compensated cardiovascular signal based on the photoplethysmographic signal may include: (i) generating, using a first finite impulse response filter, a first filtered acceleration signal based on the first acceleration signal; (ii) generating, using a second finite impulse response filter, a second filtered acceleration signal based on the second acceleration signal; (iii) generating, using a third finite impulse response filter, a third filtered acceleration signal based on the third acceleration signal; and (iv) subtracting the first, second, and third filtered acceleration signals from the photoplethysmographic signal.

In some embodiments, the method may further include: (i) storing, in a memory, a first record of the motion-compensated cardiovascular signal, and (ii) storing, in the memory, a second record of the motion signal. In such embodiments, transmitting an indication of the motion-compensated cardiovascular signal to the remote system may include transmitting an indication of the first record and transmitting an indication of the motion signal to the remote system may include transmitting an indication of the second record.

In some embodiments, the method may further include: (i) determining spectral contents of the motion-compensated cardiovascular signal; and (ii) detecting at least one peak in the determined spectral contents. In such embodiments, transmitting an indication of the motion-compensated cardiovascular signal to the remote system may include transmitting an indication of the detected at least one peak.

In some embodiments, the method may further include generating, using an analog to digital converter of the wearable device during a first period of time, a first sample of an output of a photodetector of the photoplethysmographic sensor; and (ii) determining an ambient light offset voltage based on the first sample. In such embodiments, detecting a photoplethysmographic signal may include: (a) illuminating, using a light emitter of the photoplethysmographic sensor during a second period of time, skin of a user; (b) generating, using a digital to analog converter of the wearable device during the second period of time, an offset voltage based on the determined ambient offset voltage; and (c) generating, using the analog to digital converter during the second period of time, a second sample of a difference between the output of the photodetector and the offset voltage generated by the digital to analog converter.

In some embodiments, the method may further include: (i) determining, based on the motion signal, a first activity state corresponding to a first period of time; (ii) determining, based on the motion signal, a second activity state corresponding to a second period of time, wherein the photoplethysmographic signal corresponds to the first and second periods of time; (iii) determining a first expected heart rate based on the first activity state; (iv) determining a second expected heart rate based on the second activity state; (v) determining the heart rate. In such embodiments, determining the heart rate may include determining a time-varying heart rate corresponding to the first and second periods of time, and such a determination may include (a) determining a first plurality of heart rates corresponding to the first period of time based on the first expected heart rate and the photoplethysmographic signal, and (b) determining a second plurality of heart rates corresponding to the second period of time based on the second expected heart rate and the photoplethysmographic signal. Determining time-varying heart rates corresponding to the first and second periods of time may include using a Viterbi algorithm to determine the time-varying heart rate, where the Viterbi algorithm is informed by the first expected heart rate and the second expected heart rate.

In some embodiments, determining the first activity state and the second activity state may be performed by a controller of the wearable device and transmitting an indication of the motion signal to a remote system may include transmitting an indication of the first activity state and the second activity state to the remote system. In such examples, determining the time-varying heart rate corresponding to the first and second periods of time may be performed by the remote system.

Some embodiments of the present disclosure provide a method that includes: (i) receiving an indication of a first activity state corresponding to a first period of time; (ii)

receiving an indication of a second activity state corresponding to a second period of time; (iii) receiving an indication of a photoplethysmographic signal that corresponds to the first and second periods of time; (iv) determining a first expected heart rate based on the first activity state; (v) determining a second expected heart rate based on the second activity state; (vi) determining a time-varying heart rate corresponding to the first and second periods of time; and (vii) transmitting an indication of the determined time-varying heart rate to the wearable device. In such embodiments, determining a time-varying heart rate may include: (a) determining a first plurality of heart rates corresponding to the first period of time based on the first expected heart rate and the photoplethysmographic signal, and (b) determining a second plurality of heart rates corresponding to the second period of time based on the second expected heart rate and the photoplethysmographic signal In some embodiments, receiving an indication of a photoplethysmographic signal may include receiving an indication of peaks in a spectral content of the photoplethysmographic signal. In such embodiments, determining a time-varying heart rate corresponding to the first and second periods of time includes using a Viterbi algorithm to determine the time-varying heart rate, where the Viterbi algorithm is informed by the first expected heart rate and the second expected heart rate.

In some embodiments, determining a time-varying heart rate corresponding to the first and second periods of time includes determining at least five prospective time-varying heart rates based on the photoplethysmographic signal, the first expected heart rate, and the second expected heart rate.

As used herein, a "controller" may include a variety of electronic devices configured to provide the operations described herein. In some examples, a controller may include one or more general-purpose processors configured to execute computer-readable instructions (e.g., computer-readable instructions stored in a memory of the controller or otherwise made available to the controller). Additionally or alternatively, a controller may include one or more application-specific integrated circuits (ASICs) configured to provide the described functionality (e.g., and ASIC that includes amplifiers, comparators, analog-to-digital converters, counters, oscillators, clocks, or other electronic components). A controller may include one or more electronic peripherals to facilitate operations of the controller. Such peripherals could include a memory, a memory management unit, an amplifier, a comparator, an analog-to-digital converter, a digital-to-analog converter, a counter, a multiplier, an arithmetic logic unit, an oscillator, a real time clock module, a serial communications interface, a wireless radio frontend, a display driver, a capacitive touch detector, or some other components.

Any variable or step described herein the includes making a determination "based on" some other element (e.g., a detected sensor output, some other determined or otherwise generated value or information) includes determining such a variable or performing such a step based at least in part on such other element.

These as well as other aspects, advantages, and alternatives, will become apparent to those of ordinary skill in the art by reading the following detailed description, with reference where appropriate to the accompanying drawings.

BRIEF DESCRIPTION OF DRAWINGS

The various implementations disclosed herein are illustrated by way of example, and not by way of limitation, in the figures of the accompanying drawings, in which like reference numerals may refer to similar elements.

FIG. 9 depicts an example calculation of heart rate based on calculated of motion priors.

DETAILED DESCRIPTION

Figure 1:
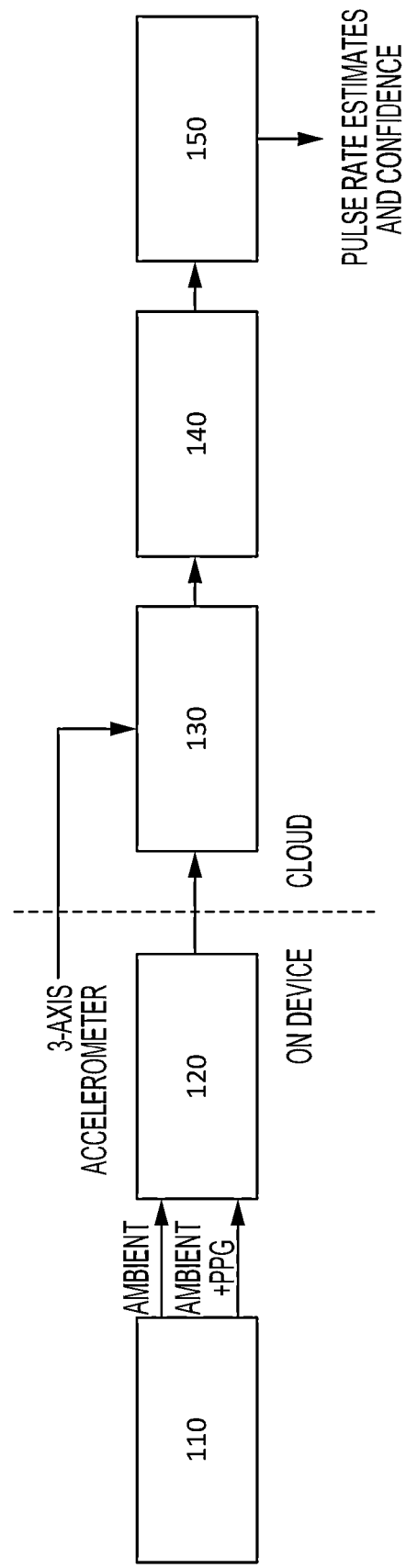
FIG. 1 illustrates an example embodiment of a method and system which extracts a heart rate signal.

This disclosure is directed at biometric devices (which may also be referred to "wearable fitness monitoring device," "biometric tracking devices," "health monitoring devices," "portable monitoring devices," "portable biometric monitoring devices" or the like) which are generally described as wearable devices. When worn, such devices gather data regarding activities performed by the wearer and/or the physiological exercise or activity state of the user. Such data can include data from the ambient environment or the interaction of the user with the environment, e.g., ambient noise, ambient light, ambient motion or user motion, air quality, etc. Also, physiological data is obtained by measuring various physiological parameters, e.g., heart rate, respiration levels, sweat, skin conductance, etc. The device is configured to extract out the true or correct heart rate from the heartbeat waveform signal observed by the monitor. This extraction is based, at least in part, on statistical prior heart rate distributions from past heart rate data. Accordingly, some signal is filtered out because the signal algorithm is not biased toward signal weight with regard to the very last incoming signal or value.

Continuous human pulse rate estimation from a wearable device can be of significant utility in understanding diseases that impact the heart. Algorithms for continuous pulse rate estimation currently have difficulty accounting for the wide dynamic range of pulse rate signals incoming under different physiologic and activity states. Thus, an algorithm capable of detecting transitions between physiologic/exercise states could incredibly useful since it would be capable of extracting an accurate or true heart rate from the incoming signal. Most importantly, the lack of heart signal in one or more expected physiologic ranges is an indicator for the onset or progression of a disease state.

The disclosure herein provides methods and devices for extracting the heart rate (HR) of a subject based on the filtering of user motion and the physiological state of the subject. The disclosure also provides methods for operating the light emitting diode (LED) and photodetector of heart rate monitors to obtain readings of the extracted heart rate value on the basis of input data unique from each user.

Finally, the disclosure provides for methods of identifying the onset or progression of a disease state in a subject.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

The present invention is directed to wearable monitoring devices having heart rate monitoring functions and methods for operating said devices. Such devices are useful for tracking the fitness, movement, and/or exercise level and/or history of a subject.

Also herein disclosed is a device utilizing an algorithm capable of detecting transitions between physiologic/exercise states using additional sensors which modulate the behavior of a pulse rate estimation algorithm to extract the true heart rate from the heartbeat waveform signal observed from a PPG. Also provided is a method and/or system for monitoring a heart rate signal in a physiologic state which indicates the relative health for the subject or the onset or progression of a disease state of the subject.

The methods and systems disclosed herein utilize contextual data to extract the true or correct pulse rates, in the PPG signal, and use a novel pulse rate estimation algorithm to determine the bias or level of compensation which must be employed in order to extract such data. This contextual data generates prior distribution(s) for pulse rate estimates that is used to extract the instantaneous pulse rate estimate reformed in the algorithm. In general, this contextual data can consist of anything that is informative for pulse rate. This can be, for example, the amount of motion the user is undergoing as determined by an accelerometer, or the activity the user is undergoing as determined by an activity classification algorithm. Other available information such as use age, weight, fitness level and demographics can also be used.

This present methods and systems create a novel pulse rate estimation algorithm based on estimates of physiologic state generated by one or more concurrently running algorithms. As an example, it is known that human pulse rates are generally centered around 100 beats per minute during the running state. Consequently, a pulse rate estimation algorithm is biased to search for a heart rate signal around 100 beats per minute, amongst the many which are simultaneously incoming. Once informed by an activity, the classification algorithm determines that the "running" physiologic state has been detected. The running physiologic state can also be determined through the processing of the accelerometer signals on the device. As another example, human pulse rates are generally centered around 50 beats per minute during the sleep state. Once again, a pulse rate estimation algorithm is biased to search for a heart rate signal around 50 beats per minute (bpm), not the least biased by which the very last incoming heart rate signal was around 50 bpm. Once informed by this activity, the classification algorithm determines that the "sleep" physiologic state has been detected.

Solving the problem this way is interesting because it enables signal filtering techniques to use physiologic priors of heart rate dynamics to extract out the true or correct pulse rate from the multitude of incoming signals or values. Consequently, the method or system dramatically improves pulse rate accuracy. Accordingly, a whole host of other physiological parameters can be extracted more accurately.

Also important, the lack of a heart signal in the expected physiologic range associated with a detected physiologic state is an indicator for the onset or progression of a disease state. One of the principal advantages is that the method can quantify signal deviation for the pulse rate dynamics of a subject.

Alternatively, the methods and systems disclosed herein can directly incorporate the use auxiliary sensor data to modify pulse rate extraction. In this way, the method or system need not actually detect the current physiologic state, nor apply a reference set of known prior on pulse rates during these physiologic states Methods and Systems for Heart Rate Monitoring The presently-disclosed monitoring device measures a plurality of physiological and exercise metrics. These metrics include, but are not limited to, the user's heartbeatwaveform, step count, total energy expenditure, calorie burn, floors climbed and/or descended, heart rate, heart rate variability, heart rate recovery, location and/or heading (by GPS, GLONASS, etc.), elevation, ambulatory speed and/or distance traveled, swimming lap count, swimming stroke type and count detected, bicycle distance and/or speed, blood pressure, blood glucose, skin conduction, skin and/or body temperature, hydration levels, respiration rate, and other physiological metrics.

In some embodiments, the monitor determines the user's stress and/or relaxation levels through a combination of one or more of heart rate variability, skin conduction, noise, and sleep. In some embodiments, the monitor determines the user's disease state, or a progression of a disease state in the user, or a medical necessity for a user, for example a regularly timed medication may need to be altered because of measurements which inform the monitor the user needs have changed. Such determinations are illustrative and not intended to be limiting.

Heart Rate Signal Collection

In some embodiments, the disclosure provide methods and devices to accurately measure heartbeat waveform for different user characteristics such as skin user motion, sweat, position, and physiologic state (e.g., skin thickness, body fat, etc.) of the users. In some embodiments, there is a mathematical relationship for correlating the heartbeatwaveform signal and heart rate which comprises taking the Fourier transform of the heatbeatwaveform signal, and then finding the frequency with the highest magnitude. This function is determined by a comparison between light intensity emitted by a light source of the heart rate monitor vs. the signal detected by the photodetector.

FIG. 1 shows flowchart for a process of operating a heart rate monitor of the present wearable fitness monitoring device. The device is configured to adjust the light emission power and/or light detection gain with a 3-axis accelerometer. Ambient light noise is subtracted by comparing the value of the received light when the light source is off as opposed to when it is on.

In some embodiments, one or more light pulses of constant and/or variable intensity and frequency are applied and used to detect the reflection of light from a user's skin. As the reflection is detected and determined, the device adjusts detection intensity and/or gain.

In various embodiments, such adjustments are executed with software, firmware or hardware.

Activity

In an embodiment, the monitoring device detects a variety of data including biometric data, environmental data, and activity data. All of this data can be presented to a user. In an embodiment, a user's heart rate may be correlated to biking speed, bike pedaling speed, running speed, swimming speed or walking speed.

Sleep States and Other Transitions

In yet other embodiments, the monitoring device automatically determines when the user is trying to go to sleep, is going to sleep, is asleep, and/or is awake or awoken from a sleep. In these cases, the monitoring device associates a combination of measured parameters/data collected such as heart rate, heart rate variability, respiration rate, galvanic skin response, motion, and/or skin temperature to determine the state of sleep. In some cases, the device also is informed by a decrease or termination of motion from the user over a given period of time.

In some embodiments, the monitoring device determines the transitions between wake, sleep, and sleep stages. In some embodiments, the monitoring device determines uses for example a batch processing or a windowed approach to classify such a transition. In certain circumstances, a decrease or increase in heart rate is indicative of such a transition.

In some embodiments, the monitoring device determines transitions using a hidden Markov model. In such cases, the change in signal occurs in, for example, user motion signal, heart rate, heart rate variability, skin temperature, galvanic skin response, and/or ambient light levels. A transition is determined by a changepoint algorithm, for instance by a Bayesian changepoint analysis.

In some embodiments, the disclosure herein is a system which includes a secondary device configured to communicate with the biometric monitoring device. Such a secondary device is capable charging the monitoring device. In some embodiments, the system includes a biometric monitoring device and a smartphone or tablet. In such embodiments, the monitoring device and the secondary device communicate through wired communication interfaces or through wireless communication such as Bluetooth, NFC, RFID, WLAN, etc.

In some embodiments, the secondary device is capable of displaying data collected from the monitor such as the user's heart rate and any other data indicative of exercise performed or health or fitness data, In another embodiment, the monitoring device automatically determines if the user is wearing the monitor. Such techniques are known to the skilled artisan such as using and providing feedback loop that determines when one or more light detectors provides too low of a return signal. And in such an event, the device reduces its power consumption.

In some embodiments, the monitoring device performs one or more operating functions upon detecting input motion on the device itself, for example, a tap, bump or swipe interaction Alarms In some embodiments, the device is a wrist-band alarm which warns the user of a medical condition or a disease state.

In some embodiments, the monitoring device is an alarm to awaken the user.

Stress & Health

In some embodiments, the biometric monitoring device determines the user's stress level health state (e.g., risk, onset, or progression of fever or cold), and/or cardiac health by calculating probabilities or combining certain measured parameters including, but not limited to, heart rate variability, galvanic skin response, skin temperature, body temperature, and/or heart rate over periods of time.

In some embodiments, the device measures data as a "baseline" as determined from input from the user. A user may qualify a certain period of time for which measurements have been taken as a "base" period in which cardiac health or other fitness parameters have improved or are at a high level. Parameters include things such as aerobic fitness or capacity, anaerobic fitness or capacity, overall inflammatory health (including bloated or painful conditions as specified by the user or a doctor whom has examined the user), and muscular fitness or strength.

PPG Amplification, Filter, & Signal Extraction

In an embodiment, the monitoring device incorporates a differential amplifier to amplify the output from the light detector. In some embodiments, the device uses a digital average or digital low-pass filtered signal which is subtracted from the output and amplified before it is digitized by the ADC. In other embodiments, an analog average or analog low-pass filtered signal is subtracted from the output. In other embodiments, the device uses a sample-and-hold circuit and analog signal conditioning circuitry.

In other embodiments, a differential amplifier also measures the difference between past and the present sample rather than measuring each signal alone. A larger gain can be applied because the magnitude of any given sample is generally much larger than the difference between any two samples and this can provide better PPG signal quality in terms of signal integration or time domain signal.

In some embodiments, the method further involves using one or more characteristics of the user's skin to adjust the heart rate monitor's gain and/or light emission intensity for filtering out signal from the user's motion. In some embodiments, the skin characteristic is based on the opacity of the user's skin.

In other embodiments, it is contemplated that any and all of the disclosed processing, extracting, and/or filtering techniques can be used in combination.

In some embodiments, the device processes signals using signal filtering and/or signal conditioning. Such methods are well known in the art and include, but are not limited to, band-pass or Butterworth filtering. These techniques are used to counteract large transients that occur. Additionally, this improves convergence. Moreover, other nonlinear filtering strategies include using neural networks or slew-rate limiting. Of course, any data received including motion, galvanic skin response, skin temperature, etc., can be used to adjust the signal conditioning.

In some embodiments, the heart rate is measured by counting the number of signal peaks within a time window or by utilizing the fundamental frequency or second harmonic of the signal (e.g., through a fast Fourier transform (FFT)). In cases where exercise is performed, FFTs can be performed on the heart rate signal acquired and then spectral peaks are extracted. This data is then processed by a multiple-target tracker which starts, continues, merges, and deletes tracks of the spectra. Such tracking operations can be achieved with single-scan or multi-scan, or multiple-target tracker topologies, joint probabilistic data association trackers, multiple-hypothesis tracking, nearest neighbor, etc. Estimation and prediction in the tracker can be done, e.g., through the use of Kalman filters, spline regression, particle filters, interacting multiple model filters, etc. A track selector module uses the output tracks from the multiple-spectra tracker and estimates the user's heart rate. This estimate then becomes a maximum likelihood track, or a weight sum of the tracks against their probabilities of being the heart rate, etc. An algorithm then further influences the selection by considering calculated pule rate priors and activity level to get the heart rate estimate. In such an embodiment, the a-prior probability of each heart rate $p_{prior}$(heart rate) based on the identified activity is retrieved from a precomputed lookup table based on data collected over a large statistically representative population. The probability of each heart rate $p_{signal}$(heart rate) is then estimated based on the observed heart rate signal, for example by taking the Fourier transform and computing the ratio between the energy at a candidate heart rate and the total energy of the Fourier transformed heart rate signal. The combined heart rate probability estimate is then formed by multiplying the a-prior heart rate probability $p_{prior}$(heart rate) with the signal based heart rate probability $p_{signal}$(heart rate).

In some embodiments, the acquisition of a true or correct heart rate is indicated to the user through a display. In other embodiments, a signal-strength indicator, viewable by the user, is represented on the display by the flashing or color of an LED. The pulsing may be timed or correlated to be coincident with the user's heartbeat.

In some embodiments, the strength of the heart rate signal may be determined by signal quality metrics such as the ratio between the magnitude of the Fourier transform of the heart rate signal at its maximal value, and the sum of the magnitudes of the Fourier transform of the heart rate signal at all other frequencies.

PPG circuitry is well known in the art and is optimized to obtain the best quality signal in the face of ambient conditions including, but not limited to, user and other object motion, ambient light, and skin color.

In some embodiments, the device includes a near-field communication (NFC) receiver/transmitter to detect proximity to other electronic devices. Such a communicator can start the function of a second device; for instance, it may launch an "app" on a mobile phone and sync sensor data to it.

In other embodiments, the monitoring device includes a location sensor which allows for a graphical representation of heart rate as a function of speed and/or geographical location. In such embodiments, the user's heart rate also can be temporally mapped in relation to speed and/or geographical location. Such data is useful in further refining the algorithm used to extract true heart rate signal. Further, such data can be allocated into different activity states or categories such as sleeping, resting, sedentary, somewhat active, medium active, and high active, and so on. Thus, a user can be informed of certain metrics of the activity state data as well as the heart rate inside that state.

Heuristic & Input Data

In some aspects, the methods and devices herein extract the heart rate from a heartbeatwaveform considering historical data of the user. For instance, a heart rate is determined with a peak count from a power spectral density graph. This heuristic approach applies a set of collected or learned historical bounds which denote the allowable rates for heart rate. These bounds are trained on a per-use or user-specific basis possessing a unique historical profile. If the determined heart rate does not fall within the bounds, and optionally considering other data collected, then the value is discarded or used to derive a true or correct heart rate on the basis of one or more probability functions. As an example, the heart rate of each user is collected when they are sitting for some period of time and which is then used as a lower bound when the user is performing a backstroke while swimming.

In an embodiment, the algorithm is tailored for each user and learns or trains the heart rate profile of the user to adapt to the user's behaviors and/or characteristics so as to more accurately extract the user's true heart rate.

In some embodiments, the invention provides a method of using input or contextual data, optionally heuristic in nature, to refine pulse rate extraction by a pulse rate algorithm. This input data produces a prior distribution for pulse rate estimates that is used to refine the instantaneous pulse rate estimate that is formed by the algorithm. The input data can consist of anything that is informative for pulse rate. The input data could be, for example, the amount of motion the user is undergoing as determined by an accelerometer, or the activity the user is undergoing as determined by an activity classification algorithm. Other available information such as user: age, weight, fitness level and demographics can also be used.

In some aspects, the device can receive user input data relating to exercise activity, food or dietary or caloric intake, body weight, body fat, medication taken, sleep period or sleep quality and/or duration, the weather conditions (e.g., temperature, humidity, rain/snow, wind, barometric pressure), ambient light, and ambient noise.

Methods of Operating

In some embodiments, the invention provides a method of operating a heart rate monitoring device having a plurality of sensors including the heart rate monitor.

Also disclosed is a method of operating a heart rate monitor of a wearable fitness monitoring device, the heart rate monitor having a light source and a light detector. In some embodiments, the method also includes adjusting and/or informing the heart rate monitor's operation(s) based on a user's motion and activity state. The method includes operating the heart rate monitor in a first mode. The first mode operation involves generating data points representing emission intensity from one or more light sources and corresponding detection levels from the light detector. The method further comprises fitting the data points of the first mode and an activity mode to a mathematical relationship relating light source emission intensity to light detector detection level, and then using the mathematical relationship to extract out the correct or true heart rate signal and also determine one or more exercise values indicative of user fitness or health. Optionally, the method also includes using the mathematical relationship to determine one or more light source emission intensity settings that identify a good performance for the heart rate monitor, and then adjusting the light source emission intensity to such a setting for operating in the first mode.

In some embodiments, the first mode and/or second mode is configured to determine one or more characteristics of the user's heartbeat waveform. These characteristics include, but are not limited to: heart rate, oxygen consumption, calories expended, blood oxygen saturation, heart waveform morphology, respiration rate and the presence of afib or other arrhythmias.

In some embodiments, the first mode and the activity mode are performed concurrently.

In yet other embodiments, the control logic of the wearable fitness monitoring device is configured to emit a succession of light pulses from a light source in a first mode.

In some embodiments, operating the heart rate monitor in the first mode involves emitting a plurality of light pulses of varying duration and intensities all simultaneously to start with, and then detecting and comparing the intensity and duration of light after interacting with the user's skin.

In some embodiments, operating the heart rate monitor in the first mode involves periodically operating the heart rate monitor in the activity mode while continuously operating the heart rate monitor in the second mode.

In some embodiments, the disclosed method for operating the heart rate monitor includes determining, from a motion detecting sensor, that the wearable device has been still for at least a defined period.

In an embodiment, adjusting the heart rate monitor's gain and/or current control logic operating in the first mode is to reduce the light emission intensity. In some embodiments, the gain and/or current control logic is adjustable by the user. In other embodiments, the gain and/or current control logic is adjusted by an algorithm. In one such embodiment, the algorithm is informed by at least the activity state of the user as determined thru measurement data received from one or more motion detection sensors.

In another embodiment, the method for operating the heart rate monitor further comprises: prior to operating the monitor in a second mode, detecting motion of the wearable device using a motion detecting sensor and/or detecting the heart rate waveform of the user using a first mode also while operating in an activity mode, and then initiating operation in a second mode of the heart rate monitor.

In yet another embodiment, the method for operating the heart rate monitor further comprises: prior to operating the monitor in a second mode, receiving input data from the user while operating in an activity mode but not detecting the heart rate waveform nor user motion in a first mode, and then initiating operation in a second mode of the heart rate monitor.

In other embodiments, the methods include adjusting the operation of a heart rate monitor of a fitness monitoring device. In such embodiments a user adjusts one or more settings for operating the heart rate monitor.

In some embodiments, operation of the heart rate monitor involves: an emission of light onto the skin of a user of the device; detecting the variation in intensity from the light which has interacted with the user's skin; and using the variation as feedback in order to adjust a gain and/or current control logic of the heart rate monitor operating in a first mode.

In some embodiments, operation of the heart rate monitor involves an emission of light pulses onto the skin of a user, one or more pulses each possessing a variable intensity with respect to other light pulses.

In yet other embodiments, operating the heart rate monitor in the first mode involves pulsing the light source at an initial frequency, and then detecting this light after it has interacted with the skin of a user.

In other embodiments, operating the heart rate monitor in the first mode involves pulsing the light source at a first and then a second frequency, and then detecting each frequency of light after it has interacted with the skin of a user. In one embodiment, the second frequency is greater than the first frequency.

In some embodiments, operating the heart rate monitor in the first mode involves determining the intensity level, duration or period, and/or pattern of two or more pulses of light. In one embodiment, a plurality of light pulses is emitted and some pulses have variable intensity and some have constant intensity. In an embodiment, a plurality of light pulses is emitted and some pulses have variable pulse duration.

In further embodiments, the control logic of the wearable fitness monitoring device is configured to operate the heart rate monitor in a first mode while also operating in an activity mode and second mode.

Methods and Systems for Identifying Disease States

Highly accurate detection of pulse rate can provide evidence of disease that can inform diagnosis, or at least trigger further clinic evaluation. Tachycardic arrhythmias would produce anomalously high pulse rates in the complete absence of motion. Since the algorithm necessarily must track motion, general cardiovascular health can be gauged by the increase in heart rate in response to motion. Drastic increases in heart rate in response to low levels of exertion indicate poor health.

Algorithm

In some embodiments, the invention provides a method of extracting a correct heart rate value from the incoming signal by modifying a pulse rate estimation algorithm based on estimates of physiologic state generated by a concurrently running algorithm.

In some embodiments, determining the intensity level, duration or period, and/or pattern of two or more pulses of light includes determining a slope of the intensity variation of light from one or more light pulses.

In some embodiments, the mathematical relationship is obtained by using an algorithm. In some embodiments, the algorithm is a Viterbi algorithm.

In some embodiments, light emission data fit to a mathematical relationship to the activity level determined. Such relationships are applied based on calculated scores between emission and detection intensity for different activity levels. In some embodiments, the mathematical relationship is $$\sum_i \alpha_i e^{-2\pi j k_i = t},$$

where j is the imaginary number, e is the natural logarithm base, and the values of $\alpha_i$ and $k_i$ are determined separately for each activity level. In still other embodiments, the mathematical relationship is based on one or more parameters selected from the group consisting of: a global maxima, a global minima, a local maxima, a local minima, an inflection point and a saddle point for multiple and/or different frequencies of light which have absorption thru the skin of a subject. In such embodiments, the mathematical relationship may include a time component. In such embodiments, the mathematical relationship may include features such as constructive or destructive interference between one or more frequencies of light.

In other embodiments, alternative mathematical relationship techniques are applied. For example neural networks can be used for predictive model building and considered by an algorithm. In still other embodiments, the device continuously and dynamically adjusts the emitted light intensity and/or gain of the photodetector.

In some embodiments, the control logic is also configured to fit the data points of the first mode to a mathematical relationship relating light source emission intensity to light detector detection level and to adjust the setting(s) of the light source emission intensity.

Device

Disclosed biometric monitoring devices can use one or more sensors with modifications or arrangements to acquire physiological or exercise data. Sensors can be modified and/or arranged with: optical reflectometer: light emitter and receiver, Multi or single LED and photodiode arrangement having wavelength tuned for specific physiological signals, synchronous detection/amplitude modulation; inertial measurement units or other motion sensors configured to detect rotation and/or acceleration of a body part (e.g., a wrist) of a user (e.g., gyroscopic sensors and/or accelerometers), GPS devices, skin temperature sensors, emg (eletromyographic sensor), ekg or ecg (electrocardiographic sensor), single-lead ecg or ekg, dual-lead ecg or ekg, magnetometers, laser doppler or power meters, ultrasonic sensor; audio sensor: strain gauge in a wrist band, wet/immersion sensor, and galvanic skin response sensor(s). Such modifications or arrangements are not intended to be limiting.

In various embodiments, the wearable fitness monitoring device is configured to perform features and operations associated with various methods and combinations thereof which are described herein.

Additionally, any and all possible combinations of any type of sensor in the proceeding list may be used as disclosed herein.

In another embodiment, the monitoring device includes an optical sensor to detect, sense, sample and/or generate data that may be used to determine information representative of, for example, stress (or level thereof), blood pressure, and/or heart rate of a user. In another embodiment, the optical sensor has one or more light sources (LED, laser, etc.) to emit or output light onto or thru the user's skin or body. In another embodiment, the optical sensor further comprises light detectors (photodiodes, phototransistors, etc.) to sample, measure and/or detect a response or reflection of light from the user's skin or body and provide data used to determine a signal that is representative of stress (or level thereof), blood pressure, and/or heart rate of a user (e.g., such as by using photoplethysmography).

In one embodiment, the wearable device comprises a heart rate monitor and at least one motion detecting sensor.

In some embodiments, the control logic of the wearable fitness monitoring device is configured to detect the motion of a user of the wearable fitness monitoring device using a motion sensor.

In yet another embodiment, the monitoring device incorporates a transimpedance amplifier stage with variable gain.

In an embodiment, the heart rate monitor is a photoplethysmographic sensor. The heart rate sensor in this embodiment will collect a photoplethysmographic signal comprising a user's heartbeat waveform. The heartbeat waveform comprises at least the heart rate of the user.

In an embodiment, the heart rate monitor is an optical heart rate monitor.

In some embodiments, the device uses a plurality of sensors which includes a motion detecting sensor. In some embodiments, the motion detecting sensor includes an accelerometer, a 3-axid accelerometer, a GPS detector, an altimeter, one or more magnetometers, or any combination thereof.

In some embodiments, the wearable fitness monitoring device comprises a motion sensor, a PPG sensor, and a control logic.

In some embodiments, the monitoring device uses a processor of the device controlled by computer-executable instructions stored in memory. In some embodiments, this function is executed by an electrical circuit. The following are some examples of hardware that can perform this execution: field-programmable gate arrays (FPGAs) and application specific integrated circuits (ASICs). Also, general-purpose microprocessors may be used.

In general, processors of the present disclosure are coupled with memory that stores executable instructions for control.

In some embodiments, the PPG sensor comprises: a periodic light source, a photo-detector positioned to receive light emitted by the periodic light source after interacting with the skin of a user, and circuitry for transmitting the output of the photo-detector.

In some embodiments, the disclosure provides a wearable fitness monitoring device comprising: a motion sensor configured to provide output data comprising the motion by a user wearing the device; and a photoplethysmographic (PPG) sensor.

The PPG sensor may include, but certainly is not limited to: a periodic light source, a photo detector, which may be positioned such that it receives the emitted light only after the light has interacted with a user's skin, and circuitry for transmitting data.

In some embodiments, the periodic light source is an LED.

In other embodiments, the light detector has a threshold detection level on the basis of a pre-determined signal to noise ratio.

In some embodiments, the monitoring device uses a processor of the device controlled by computer-executable instructions stored in memory. In some embodiments, this function is executed by an electrical circuit. The following are some examples of hardware that can perform this execution: field-programmable gate arrays (FPGAs) and application specific integrated circuits (ASICs). Also, general-purpose microprocessors may be used.

In general, processors of the present disclosure are coupled with memory that stores executable instructions for control.

In yet other embodiments, the photoplethysmographic sensor optionally includes an in-mold labeling (IML) film over the photo detector and the light source.

In an embodiment the device allows for the collected data to be viewed. For instance, one can view the data using a web browser or other network-based application. The present biometric monitoring device can collect and store data and then can transmit the data to an account on a web service, computer, mobile phone, or other electronic station where the data may be further stored, processed, and/or visualized.

In some embodiments, the monitoring device is connected to other devices. For example, devices such as an outside EKG sensor on a chest strap or a GPS receiver in a smartphone (providing position data) are within the scope of the present invention. The monitoring device communicates with these other device(s) using either wired or wireless communication.

Optical Sensor(s)

In other embodiments, each and any of the optical sensors are on the interior or skin-contacting side of the biometric monitoring device. In other embodiment, one or more of the optical sensors are on one or more non-skin-contacting side of the monitoring device. Such sides of the device contact the outside environment.

In some embodiments, the monitoring device contains a band that holds the other components of the device to the skin of the user.

In some embodiments, the monitoring device contains a display and wristband. In some embodiments, the monitoring device contains mounted buttons.

In some embodiments, the user can press buttons to take an instantaneous heart rate measurement. Additionally, the display can show whether or not the measurement is detected and/or the measurement of the user's heart rate.

In another embodiment, measurements from the optical sensors are demonstrative of physiological data and/or environmental data.

In some embodiments, the monitoring device detects reflected light and/or light emitted light from the skin of the user. In some embodiments, the monitoring device contains light sources and light detectors that arranged in an array or pattern that enhances the signal-to-noise ratio. In some embodiments, the sensors on the monitoring device collect data such as a user's heart rate, respiration volume and/or rate, variability of a users' pulse or heart rate, the user's oxygen saturation (SpO2), blood volume, and skin moisture.

In some embodiments, the monitoring device employs one or more light source(s) that emit light having one or more wavelengths that are directed to a type of physiological data to be collected. Also, the optical detectors measure, sample, and/or detect one or more wavelengths directed to a type of physiological data. In one embodiment, an LED light source emits light in the wavelength of green and a photodiode is positioned to sample, measure, and detect a response and/or reflection of the light which is used to determine the user's heart rate. In one embodiment, an LED light source emits light in the wavelength of red and photodiode is positioned to sample, measure and detect a response and/or reflection of the light which is used to determine SpO2. In certain embodiments, he color or wavelength of the light emitted by the light source is adjusted and/or controlled.

In some embodiments, the monitoring device includes a window residing in the housing so that the device can optimize optical transmission. The window permits emitted light onto the skin of the user and a reflection of that light to pass back through the window for measurement.

In some embodiments, the monitoring device includes light pipes or other light-transmissive structures for transmission of light. Scattered light from the user's body may be directed back to the optical circuitry in the device through the same or adjacently positioned similar assemblies. Certain optical designs of the present disclosure minimize low light loss and thereby improving the signal-to-noise-ratio.

In some embodiments, the light pipes or similar assemblies include a material that selectively transmits light of one or more specific wavelengths with higher efficiency than the other wavelengths in order to filter light. Such a bandpass filter is capable of tuning the signal to improve specific physiological data type. For instance, an In-Mold-Labeling or "IML" light-transmissive structure may be implemented with material so as to pass infrared light with greater efficiency than light of other wavelengths. In other embodiments, the monitoring device includes a light-transmissive structure having an optically opaque portion. These types of assemblies can be provided by a double-shot molding process wherein opaque material and transparent material are separately injected into a mold. Such a device with a light-transmissive assembly filters varying wavelengths depending on the direction of light travel through the light-transmissive assembly.

In another embodiment, the reflective assemblies are placed in the field of view of the light emitter(s) and/or light detector(s). Holes that channel light from one or more emitter(s) and to one or more detector(s) are covered with reflective material (e.g., chromed). Reflective material increases the efficiency with which the light is transported to the skin. The hole may be covered with for example an optical epoxy to prevent liquid from entering the device.

In an embodiment, the PPG light source and photodetector geometry calls for two light sources placed on either side of the photodetector.

In an embodiment, light pipes ensure that one or more LEDs and one or more photodetectors contact with the surface of the user's skin. Some of the light is scattered off of blood in the body while some is reflected back to the photodetector.

In an embodiment, the ends of the light pipes which are in contact with or otherwise are mounted toward the user's skin are contoured. This contouring can either focus or defocus light depending on the desired optimal PPG signal. Emitted light can be focused at a depth over an area of certain blood such that a vertex of these foci overlaps and the photodetector detects an optimal amount of scattered light.

In some embodiments, the biometric monitoring device can include a concave or convex shape. In some embodiments, the device light pipes selectively and controllably route light, further into a shape, say that of a cylinder possessing an axis parallel to the skin-side which improves the signal-to-noise-ratio by increasing the efficiency of light transferred.

In other embodiments, the device uses light source(s) and/or detector(s) which are mounted on a Flat Flex Cable or "FFC" or flexible PCB.

In other embodiments, the device is worn or carried on the body of a user. In such embodiments, the device includes a wrist-worn or arm-worn band or bracelet In other embodiments, the device consists of a metal material surrounded by housing. Materials that shield and house the components of wearable devices such as these are well known in the art and it is within the purview of the skilled artisan to make minor adjustments in assembly as necessary for the device to function optimally.

In other embodiments, the signal received from the user's skin is digitized by an analog to digital converter (ADC). The intensity of the light intensity from one or more light sources can be modified, for instance reduced, to avoid saturation of the output signal. Accordingly, an active control of the system like that of a proportional-integral-derivative (PID) control, fixed step control, predictive control, or a neural network is utilized to handle data derived from sensors in the device such as motion, galvanic skin response, etc.

In another embodiment, the monitoring device uses an array of photodiodes or a CCD camera. Such an array is in contact with the skin or offset by a small distance.

In another embodiment, the device uses a plurality of photodetectors and photoemitters plotted at irregular or regular distances along a surface which is in contact with the user's skin. Any signal-quality metric associated with a given site is optionally disabled.

In another embodiment, the device includes a plurality of sensors such as optical, acoustic, pressure, electrical (e.g., ECG or EKG), and motion.

Each and any of the sensors discussed throughout this disclosure can be used in conjunction with other sensors.

In other embodiments, the device includes galvanic skin-response (GSR) circuitry to measure the signal from the skin of a user which correlates or is representative of physiological changes.

Processors

In another embodiment, the monitoring device includes one or more processors. Processors are used to store and execute applications that use acquired sensor data. Any and all processors can each have a combination of one more sensors directly connected. Each sensor and processors can exist as discrete chips or in the same packaged chip (multi-core).

In an embodiment, the monitoring device includes one or more processors placed on a daughterboard consisting of all of the analog components. Daughterboards have some electronics which are typically found on a main PCB, these include, but not limited to, filtering circuits, sample-and-hold circuits, transimpedance amplifiers, level shifters, and a microcontroller unit. The daughterboard is connected to the main PCB through a digital connection or an analog connection. In other aspects, the daughterboard is connected to the main board through one or more flex cable or wires.

In other embodiments, multiple applications are stored on one or more processors. Herein it is contemplated that an application (app) can be any executable code and/or data. Such data can be graphics or other information including an output generated by one or more applications. Also disclosed herein, the executable code and/or data can reside on one or more processors or memory or any combination thereof. External memory includes, but is not limited to, NAND flash, NOR flash, flash on a separate or remote processor, mechanical or optical disks, RAM, etc.

In other embodiments, a request to execute an application is received by an application processor which retrieves the executable code and/or data from the external storage and executes it. Executable code can be permanently or temporarily stored on one or more processors or the memory. Moreover, a processor can retrieve and/or execute only the portion of executable code.

Herein disclosed, the application can be loaded onto one or more processors and/or any external storage via a variety of wired, wireless, optical, or capacitive modes including, but not limited to, USB, Wi-Fi, Bluetooth, NFC, RFID, Zigbee.

In some embodiments, one or more sensors and processors are integrated with one another and share components or resources.

In some embodiments, a hybrid antenna is included that combines a radio frequency antenna (Bluetooth antenna or GPS antenna) with an inductive loop. Such antennae are used in a near-field communications (NFC) tag or in an inductive charging system.

Charging and Data Transmission

Some embodiments of biometric monitoring devices can use a wired connection to charge an internal rechargeable battery and/or transfer data to a host device such as a laptop or mobile phone. In another embodiment, the biometric monitoring device contains one or more electromagnets and the charger or dock for charging and data transmission contains an electromagnet and/or a permanent magnet. The monitoring device is configured (e.g., a processor in the charger or dock may be configured via program instructions) to turn one or more electromagnets on when the monitoring device is connected for charging.

Data Transfer

In some embodiments, the monitoring device includes a communications interface that executes at least two differing protocols possessing differing data transmission rates. Other such adaptive data transmission techniques and functionality are encompassed within the present disclosure and are well known in the art.

Apps

In some embodiments, the monitoring device is a watch and/or a bracelet, armlet, or anklet factor which is programmed with "apps" that deliver a certain desired function and/or display desired data. The skilled artisan is very capable of configuring the software and hardware necessarily coupled to the processors and sensors of the present device. Such methods of assembling these components of wearable devices are known in the art.

User Interface

In some embodiments, the device includes interface functionality which allows one or more methods of interacting with the device either locally or remotely.

In some embodiments, the device transmits data onto a digital display. Examples of such display technologies are one or more of LED, LCD, E-Ink, Sharp display technology, AMOLED, TN, HTN, STN, FSTN, TFT, IPS, and OLET. The display shows data stored locally or remotely. The device also uses a sensor an Ambient Light Sensor ("ALS") to control or adjust the amount of screen backlighting, if used.

In another embodiment, the device can use single or multicolor LEDs to indicate measured states representative of heart rate or other physiological data.

In some embodiments, an E-Ink display puts the device in an "always-on" state that does not drain the battery life significantly.

In some embodiments, the device communicates information with one or more physical motions from the device. In such an embodiment, the device uses a vibration-inducing motor, and optionally in combination with other motion providing technology.

In some embodiments, the device communicates information with audio feedback.

Each example is provided for illustration and is not intended to limit the scope of information that may be communicated by such embodiments of the monitoring device.

In some embodiments, the device receives activity state or exercise input data from the user locally or even remotely. The user can input the activity or exercise that the user is performing or did perform within a given period of time. In one embodiment, the user interface buttons are pressed by the user to scroll thru an available list of activity states or exercises. In other embodiments, input is given with audio commands. All input methods can be communicated into the monitoring devices locally or remotely.

Wireless

The monitoring devices can include a method for wireless communication. To transmit and receive information the device uses one or more of interfaces including: Bluetooth, ANT, WLAN, power-line networking, and cell phone networks. These are examples and do not limit using other existing wireless communication methods or protocols, or wireless communications techniques or protocols yet to be invented.

The wireless connection can be bi-directional. The monitoring device can transmit, communicate and/or push data to other devices such as smart phones, computers, etc., and/or the Internet and connected servers. The device can also receive or request data from the other devices and/or the Internet.

In some embodiments, the device can relay communication to other devices.

The monitoring device can present data on the display for examples:

Historical graphs of heart rate and/or other data measured, stored locally or remotely (such as from an account on the cloud or on a website).

Historical graphs of user activity and/or sleep data that are measured stored locally or remotely.

Coaching and/or dieting data based on collected user data.

User progress toward heart rate, activity, sleep, and/or other user-desired goals.

Summary statistics, graphics (such as emoticons), badges, or metrics (such as grades) to describe the aforementioned data Social content such as Facebook updates or Twitter feeds Comparison data between the user data and similar data for his/her "friends"

In various embodiments, the monitoring device uses NFC, RFID, or other short-range wireless communication circuitry.

These examples are provided for illustration and are not intended to limit the scope of data that may be transmitted, received, or displayed by the device, nor any intermediate processing that can occur during such transfer and display.

Device Connections

The portable biometric monitoring device disclosed herein collects one or more types of physiological and/or environmental data from embedded sensors and/or external devices and is capable of communicating the information to other devices. Also included in the environmental data are internet-accessible data sources.

OTHER EMBODIMENTS

In one embodiment, a system for monitoring and reporting the fitness level and/or one or more physiological values of an individual comprises:
  a. a wearable device comprising:
    i. a housing,
    ii. one or more motion detection sensors and a heart rate monitor sensor,
      wherein each sensor resides in the housing and generates data from one or more signals indicative of physiological parameters of the individual when the device is worn by the individual;
    iii. a display, residing on the housing, and configured to receive and display data from a computing device and/or a remote server, and
    iv. one or more processors, residing in the wearable device, in communication with each sensor,
      wherein the processor is configured to: receive data from one or more sensors comprising the signal data, transform the signal data, and send the transformed data set to a computing device and/or to a remote server;
  b. one or more computing devices, optionally physically separate from the wearable device, in communication with the processor and the display, configured to:
      receive data from the processor(s) and/or the computing device,
      extract out a second data set from the transformed data set and use an algorithm to generate one or more fitness or physiological parameters based on at least one probability function and input data comprising activity state of a user.

In one embodiment, the system further comprises a remote server, in communication with the processor(s) and computing device, and configured to:
  receive data from the processor(s) and/or computing device,
  extract out a second data set from the transformed data set and use an algorithm to generate one or more fitness or physiological parameters based on at least one probability function and input data comprising activity state of a user.

In one embodiment, the system further comprises a galvanic skin response (GSR) sensor.

In one embodiment, the computing device and/or remote server sends one more graphical presentations and/or recommendations to the display.

In one embodiment, the second data set is extracted from the transformed data using a Viterbi algorithm informed by at least one function computing the statistical prior for pulse rate transitions.

In one embodiment, the remote server and computing device each upload and download transformed data continuously.

In one embodiment, the computing device is configured to use an algorithm to predict at least the top five most probable pulse rate paths.

In one embodiment, the motion detection sensor comprises a global positioning system (GPS).

In one embodiment, one or more motion sensors comprises a 3-axis accelerometer.

In one embodiment, the accelerometer is configured to be sampled at 50 Hz, optionally stored to a flash drive and/or optionally reported to the cloud, and wherein the each accelerometer is configured to subtract a PPG signal successively by FIR filtering.

In one embodiment, a method of operating a heart rate monitor of a wearable fitness monitoring device, the heart rate monitor comprising one or more light sources, a motion detection sensor, and one or more light sensors, the method comprises:
  (a) operating the heart rate monitor in a first mode, in an activity mode, and in a second mode,
  (b) determining an accurate value for one or more physiological parameters using an algorithm based on at least one probability function and input data comprising activity state of a user, wherein:
  the first mode is configured to detect ambient light along with the heartbeat waveform and motion from a user, wherein the first mode generates a signal data set representing emission intensity from one or more light sources and corresponding to detection levels from the one or more light sensors, and communicates the signal data set to the second mode,
  the activity mode is configured to receive input data from the user and/or from one or more motion detection sensors, wherein the activity mode generates an activity data set comprising the activity state of the user, and communicates the activity data set to the second mode,
  the second mode is configured to receive data from the activity mode and first mode, wherein the second mode generates a modified data set by extracting data from the signal data set of the first mode which is collected from a photoplethysmographic (PPG) light sensor.

In one embodiment, the algorithm is a Viterbi algorithm informed by at least one function computing the statistical prior for pulse rate transitions.

In one embodiment, the algorithm predicts at least the top five most probable pulse rate paths.

In one embodiment, one or more motion detection sensors is a 3-axis accelerometer which is sampled at 50 Hz, optionally stored to a flash drive and/or optionally reported to the cloud, and wherein the each accelerometer component is configured to subtract a PPG signal successively by FIR filtering.

In one embodiment, the method for extracting one or more corrected heart rate values of an individual from sensor data, comprises:
 obtaining a signal data set by detecting ambient light along with the heartbeat waveform and motion from an individual;
 obtaining an activity data set by receiving input data from the individual and/or from one or more motion detection sensors;
 communicating the signal data set and activity data set to a computing device;
 using a computing device to generate a modified data set by extracting data from the signal data set comprising signal data from a photoplethysmographic (PPG) light sensor and from the activity data set by using an algorithm informed by at least one statistical prior for pulse rate transitions;
 using the modified data to generate one or more probable pulse rate paths;
 using at least one path to generate one or more corrected heart rate values of a subject.

In one embodiment, the method further comprises storing the one or more corrected heart rate values on a flash drive and/or on a cloud system.

In one embodiment, a computing device, residing on or optionally physically separate from a wearable device, is capable of communication with one or more sensors, processors, and with a display on the wearable device, and optionally in communication with a remote server, configured to:
 receive data from one or more of the sensors, processors, and/or a remote server;
 determine an accurate value for one or more physiological parameters from received data, comprising data representing collected sensor data, using an algorithm to generate one or more fitness or physiological parameters based on at least one probability function and input data comprising activity state of a user,
 wherein the computing device is configured to extract out a second data set, from the received data set, which is used by the algorithm.

In one embodiment, the algorithm is a Viterbi algorithm.

Determining spectral contents of a signal could include performing a Fourier transform, a wavelet transform, determining the power of the signal in one or more bands of frequencies, or determining some other information about the magnitude, phase, amplitude, coherence, or other properties of the signal as a function of frequency. Determining spectral contents of a signal could include determining a plurality of frequency components of the signal. Such spectral contents could include and/or be indicative of peaks, local maxima, troughs, local minima, rising edges, falling edges, or other features of a function relating the amplitude or other properties of the signal and frequency.

In one embodiment, a remote server is in communication with one or more sensors, processors, a display, and optionally a computing device, each of which reside on a wearable monitoring device, configured to:
 receive data from one or more of the sensors, processors, and/or a remote server;
 determine an accurate value for one or more physiological parameters from received data, comprising data representing collected sensor data, using an algorithm to generate one or more fitness or physiological parameters based on at least one probability function and input data comprising activity state of a user,
 wherein the remote server is configured to extract out a second data set, from the received data set, which is used by the algorithm.

It should be noted that this disclosure is drafted in the context of a biometric monitoring device, but also encompasses any and all other devices that have the same or suitable hardware and perform the same function.

There are many concepts and embodiments described and illustrated herein. While certain embodiments, features, attributes, and advantages have been described and illustrated herein, it should be understood that many others, as well as different and/or similar embodiments, features, attributes and advantages are apparent from the description and illustrations. As such, the above embodiments are merely provided by way of example. They are not intended to be exhaustive or to limit this disclosure to the precise forms, techniques, materials and/or configurations disclosed. Many modifications and variations are possible in light of this disclosure. It is to be understood that other embodiments may be utilized and operational changes may be made without departing from the scope of the present disclosure. As such, the scope of the disclosure is not limited solely to the description above because the descriptions of the above embodiments have been presented for the purposes of illustration and description.

Importantly, the present disclosure is neither limited to any single aspect nor embodiment, nor to any combinations and/or permutations of such aspects and/or embodiments. Moreover, each of the aspects of the present disclosure, and/or embodiments thereof, may be employed alone or in combination with one or more of the other aspects and/or embodiments thereof. For the sake of brevity, many of those permutations and combinations will not be discussed and/or illustrated separately herein.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

FIG. 1. diagrams the system and general method by which the present device extracts a true or correct heart rate from an observed PPG signal. An automatic gain and current control 110 module outputs an ambient light signal and a signal that is the sum of an ambient light signal and a PPG signal. Another module 120 then generates a PPG signal by subtracting the ambient light signal from the sum signal. A motion compensation module 130 then compensates the generated PPG signal to account for user motion. Another module 140 then generates spectrogram and pointwise pulse rate probabilities from the compensated PPG signal. A pulse rate path estimation module 150 then uses the Viterbi algorithm to calculate past transition probability priors as they are associated with input data as to the activity state of the user at that time. With this information, the algorithm calculated the probability of one or more heart rate paths and extracted a true heart rate from the signal on the basis of confidence limits for these pathway estimates.

Note that the illustration in FIG. 1 of certain functions being performed on a device, while other functions are performed by a server or other remote system in communication therewith, is intended as a non-limiting embodiment. Different divisions of operations between wearable devices and remote systems (e.g., servers) in communication therewith are contemplated. In some examples, certain operations may be performed on a wearable device in order to reduce a bandwidth or other measure of communications usage for an uplink to the remote system. For example, the wearable device could determine, from an accelerometer signal or other motion signal that is indication of activity of a wearer, an activity state or other information indication of a motion or activity of the wearer. The wearable device could then transmit an indication of such determined activity or motion information. In another example, the wearable device could perform a spectral analysis (e.g., determine a Fourier transform and extract information about peaks or other features thereof), a compression, or some other analysis on a detected photoplethysmographic (PPG) signal and could transmit the results of such analyses to a remote system, e.g., to reduce the bandwidth of the uplink to the remote system. Additionally or alternatively, a motion signal (e.g., an accelerometer output), a PPG signal, or some other signal could be transmitted to the remote system without any such compression or preprocessing, and the remote system could use those signals to perform some analyses (e.g., to use the motion signal to generate a motion-compensated PPG signal from the PPG signal).

Figure 2:
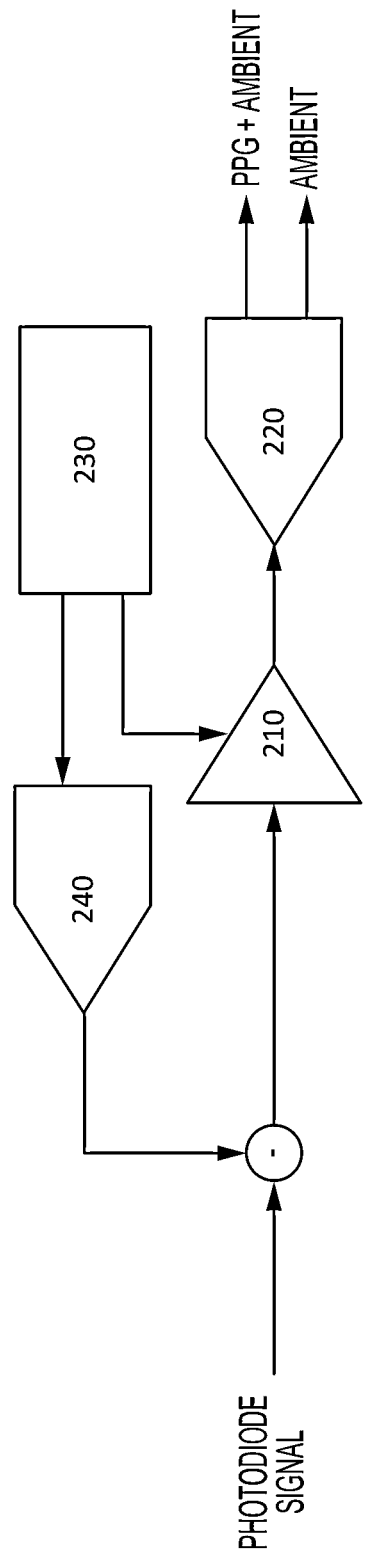
FIG. 2 illustrates an example embodiment of automatic gain and current control.

In FIG. 2, a signal comprising ambient light, motion noise, and the heartbeat waveform of the user of the wearable device was detected by a photodetector ("photodiode signal" in FIG. 2). Any such signal must be adjusted because it carries many unwanted components. Among the specific components that need filtering are: skin reflected light from the light emitting diode (LED), ambient light alternating current (AC) component due to e.g. arm swing while running, and an ambient light direct current (DC) component. If the settings of an analog front-end (AFE) 210 are not configured correctly these unwanted components can occupy the entire analog-to-digital converter (ADC) 220 range. The signal of interest, photoplethysmogram (PPG), can be lost under the AFE thermal noise and ADC quantization noise. A device samples both the PPG and ambient light channels with the same AFE settings. Thus, the goal is to extract signals of interest which occupy full range of ADC, minimize AFE thermal noise and quantization noise relative to signal(s) of interest, maximize sign to noise ratio (SNR).

To meet these goals, the automatic gain and current control logic 230 was configured to adjust ambient light digital-to-analog converter (AMBDAC) 240 current to remove DC component from signals of interest (skin reflection from LEDs, ambient light DC component) and to adjust amplifier 210 gain prior to ADC 220. The adjustment or adaptation rate in the configuration of FIG. 2 is fast enough to prevent clipping of signal when sudden shift in DC level due to e.g. blood pooling in pleth (DC drift), or sudden shift in ambient light level and is slow enough not to introduce too many discontinuities in signal of interest (this method can digitally compensate for changes in gain and ambient light DAC 240 current but variations in components always leave some residual shift). The setup in FIG. 2. provides settings which are shared for both pleth (LED on) channel and ambient light (LED off) channel. Further, these settings minimize AFE 210 noise while preventing clipping for both channels.

Figure 3:
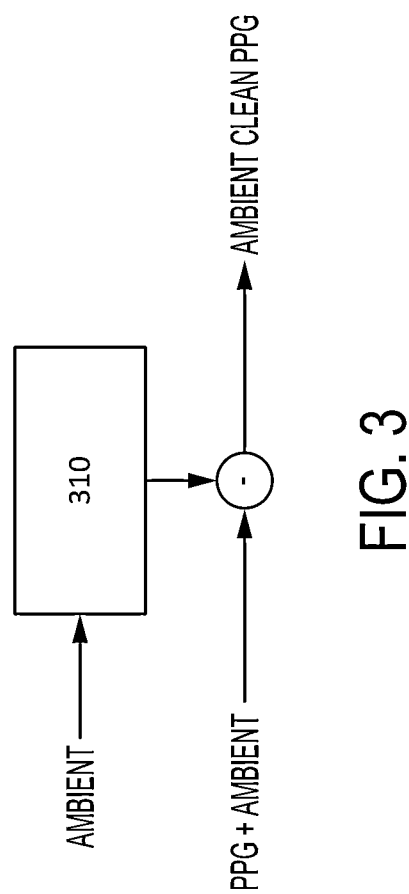
FIG. 3 provides an example embodiment of ambient light subtraction.

As discussed above, ambient light changes significantly during arm swing in bright sunlight as light pipes follow through wrist tissue on either side of the device into the photodiode. This causes periodic corruption of the PPG signal and can lead to pulse rate estimates at the arm swing rate. The configuration in FIG. 3. provides for light which was sampled at a 50 Hz sampling period for each duty cycle in two channels: the PPG channel (LEDs on, "PPG+Ambient" in FIG. 3) where the photodiode measures pleth+ambient light and an ambient light channel (LEDs off, "Ambient" in FIG. 3) where the photodiode measures ambient light only. This configuration uses an interpolation module 310 to interpolate the ambient light channel to PPG timestamps and subtracts ambient light while the clean PPG channel was stored on a flash drive and/or sent to a remote server or the cloud.

Figure 4:
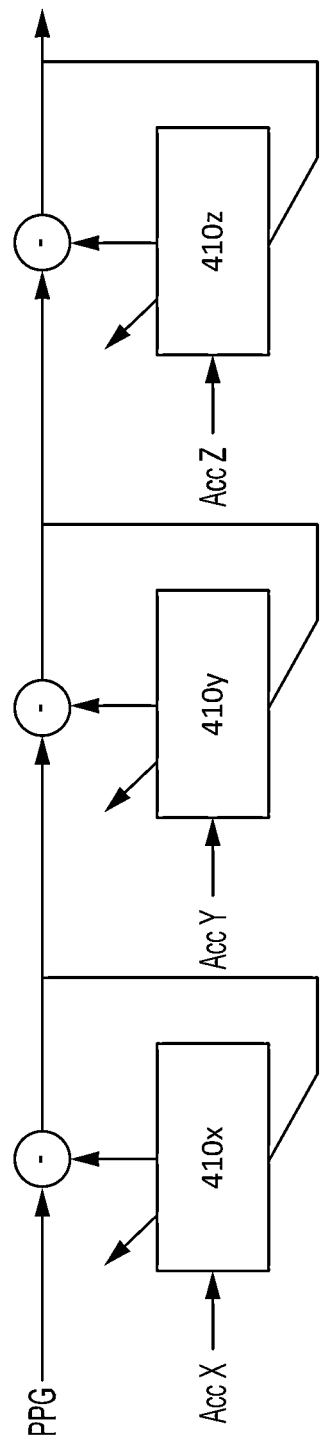
FIG. 4 provides an example embodiment of motion compensation.

Motion artifacts cause significant corruption of the pulse rate value if not compensated for. FIG. 4. employs a 3-axis accelerometer (outputs indicated by "AccX," "Acc Y," and "Acc Z" in FIG. 4) which was sampled at 50 Hz duty cycles and stored to a flash drive and/or reported to a remote server or the cloud. From there, a Least mean squares (LMS) algorithm was applied to subtract the finite impulse response (FIR) filtered version of each accelerometer component (Adaptive FIR filters 410$x$, 410$y$, and 410$z$) from the PPG. The additive value of three such adaptive filters 410$x$, 410$y$, 410$z$ culminates in the removal of almost any component from the accelerometer correlated with the PPG.

Figure 5:
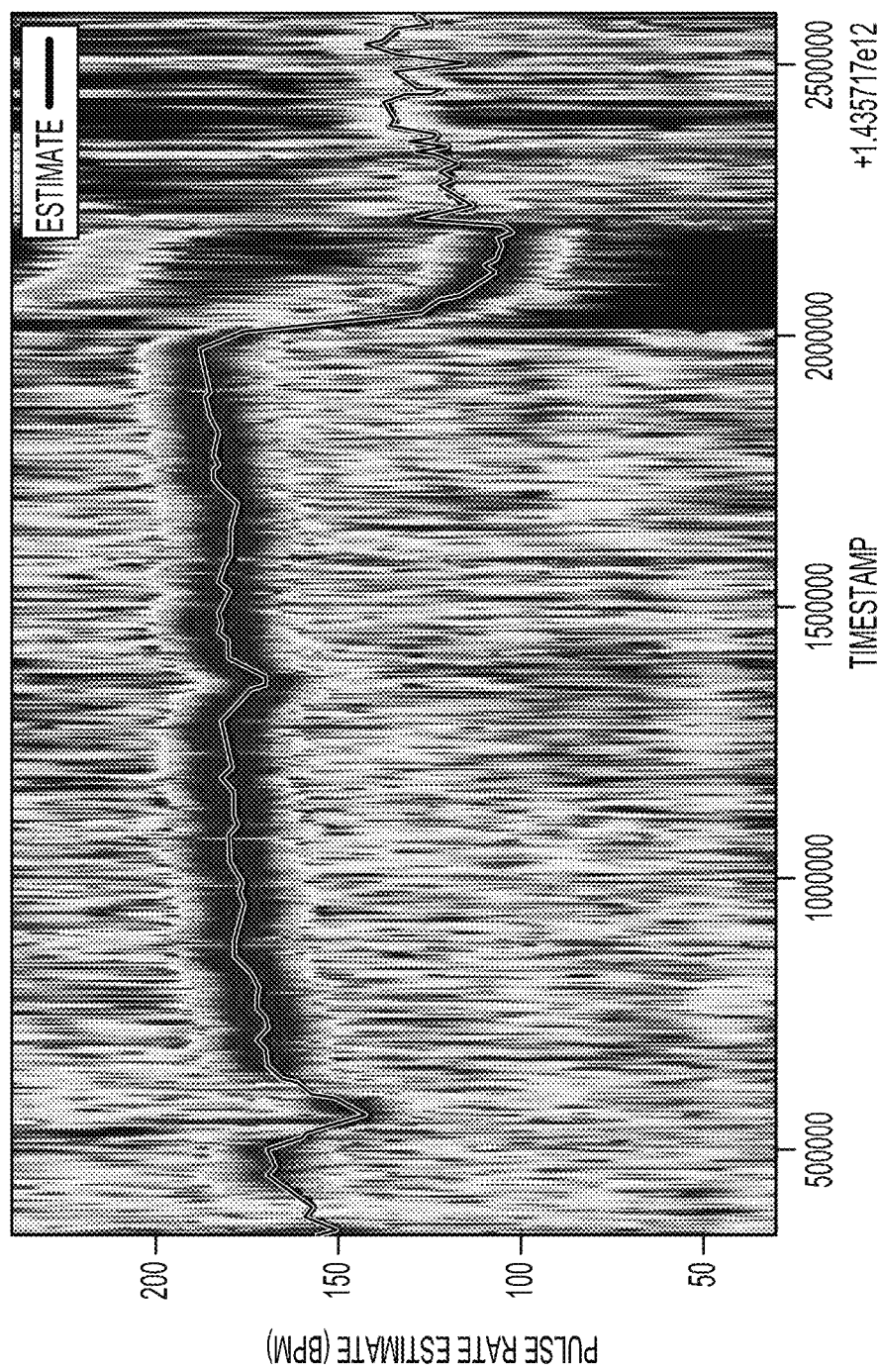
FIG. 5 provides an example spectrogram and an overlaid estimated pulse rate determined from an observed PPG signal.

FIG. 5. illustrates the calculated probabilities from the obtained motion-compensated PPG spectrogram. As depicted, the signal spectral content was charted as it evolved over time. The algorithm computed the probability of observing PSDt, at a given point in time, t, if pulse rate is prt by dividing energy, at prt, by total energy. This definition can be represented by:

$$P(PSD_t|pr_t) = PSD_t[pr_t]/\Sigma_k PSD_t[k]$$

As is expected though, a heart or pulse rate varies continuously over time. So, the algorithm took this into account by computing statistical priors for pulse rate transitions. The probability pulse rate goes from prt→prt+1: a (prt, prt+1). This is combined with probability of observing PSDt, if pulse rate is prt: P(PSDt|prt). The probability of a pulse rate, k, at time, t, allows for Vt,k, which is then computed by: $V_{t,k} = \max_x P(PSD_t|k) \cdot a(x, k) \cdot V_{t-1,x}$. Dynamic programming with the Viterbi algorithm generated one or more likely pulse rate paths over the analysis period plus a confidence interval (probability) for each path. These priors and pathways prevent the heart or pulse rate estimate from locking onto harmonics of PPG or onto residual motion artifacts. Moreover, this allows pulse rate to be estimated during periods of low signal quality.

Figure 6:
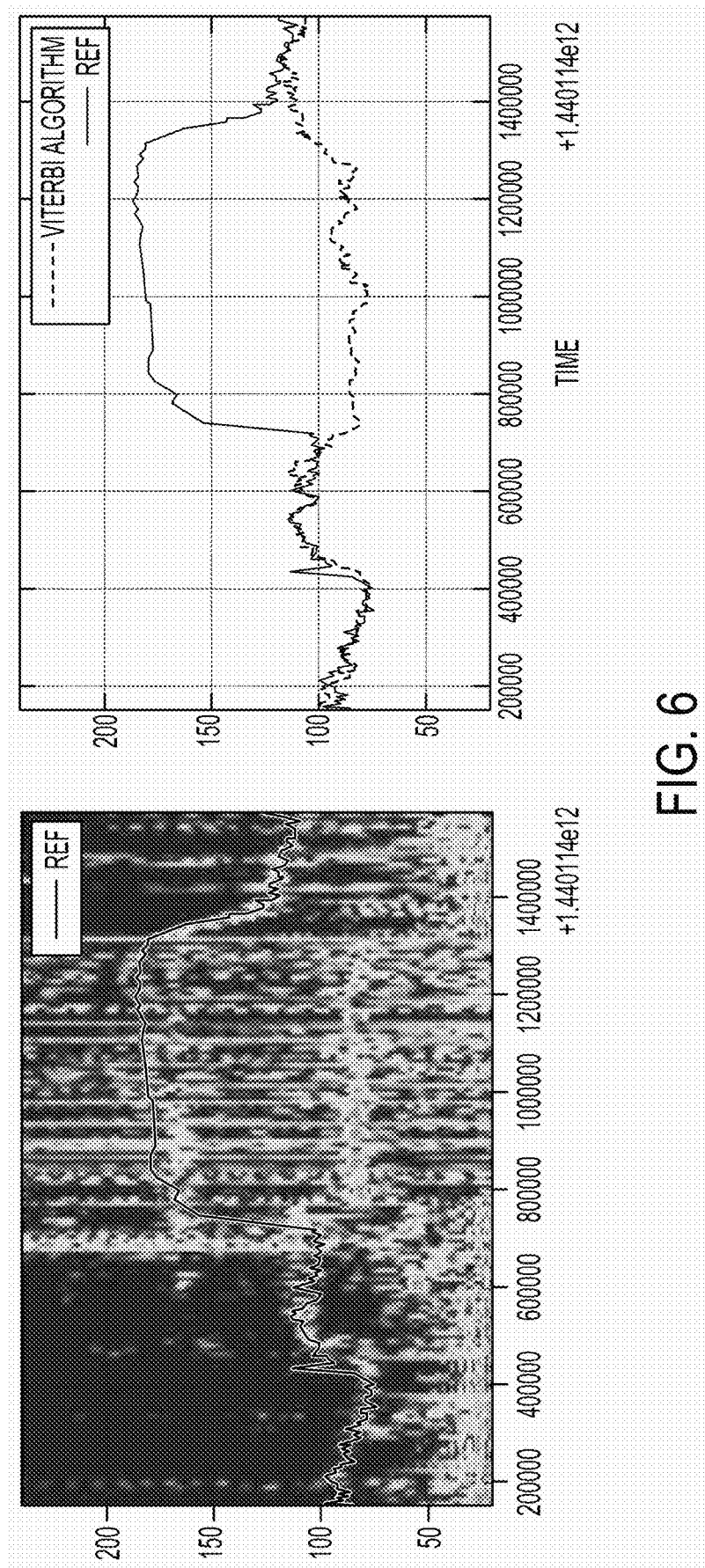
FIG. 6 depicts an example spectrogram and the calculation of motion priors from a PPG signal that includes noise.

Pulse rate or heart rate transitions are typically missed during exercises such as from walking to running. FIG. 6. depicts an estimation algorithm which has locked on to lower harmonics of an observed PPG signal. Additionally, it is easy to see that the signal quality during running is poor.

This biases the algorithm to prefer to stay close to its current estimate (higher weight given to prior) in these conditions and pick, then extract out the higher or lower biased heart rate signal.

Figure 7:
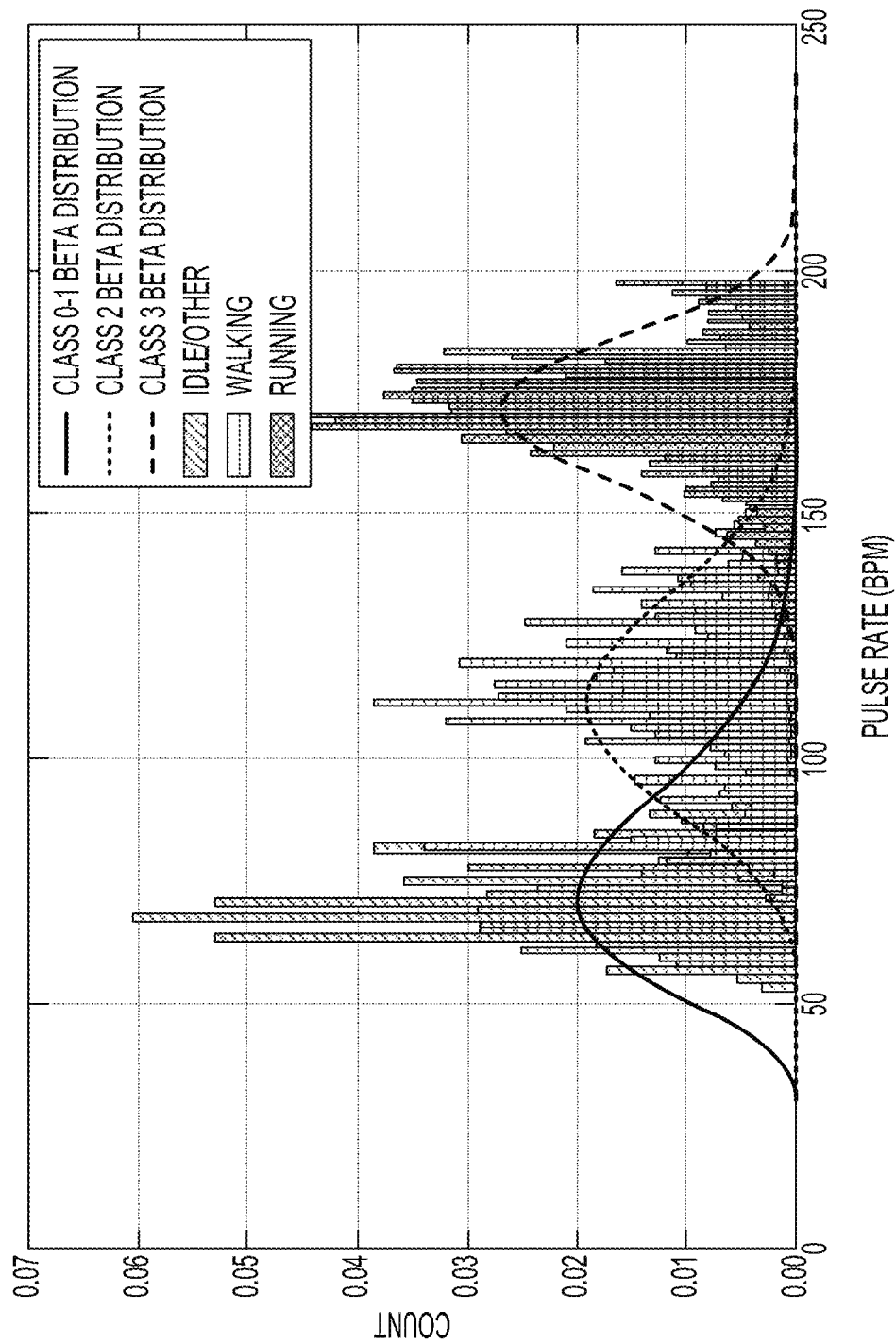
FIG. 7 depicts an example embodiment of the calculation of motion priors for different physiological states of exercise of an individual.

FIG. 7. shows the distributions for different physiological exercise states of the user. Given that an individual is running, we know something about their likely pulse rate and their likely pulse rate path. These distributions make up data which, along with other measurements taken, forms the prior for pulse rate path and estimation. Group pulse rate estimates were calculated and then based on activity class (idle, walk, run). Next, each activity class was fit to a beta distribution. The algorithm then added one or more regularization functions (e.g. don't allow distribution to have probability<0.1 at any pulse rate) to prevent overfitting of prior because our datasets are small (<100 people).

Figure 8:
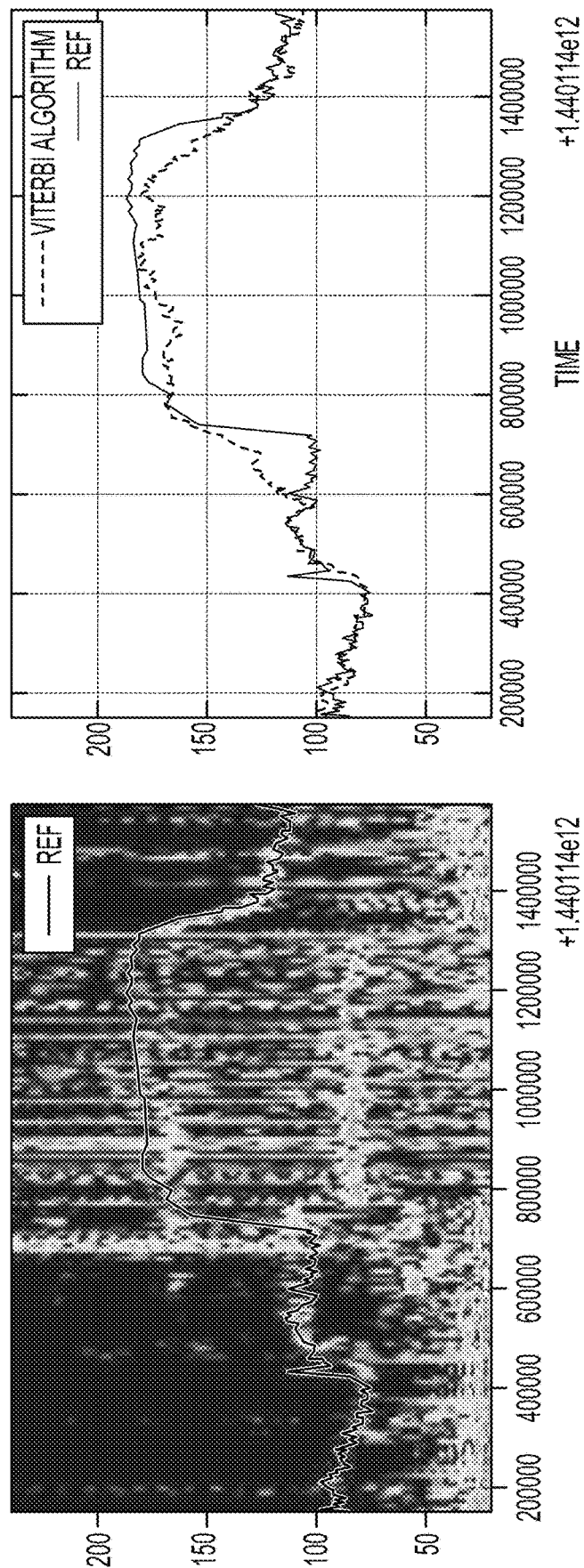
FIG. 8 depicts an example calculation of heart rate based on calculated of motion priors.

FIG. 8. illustrates the result of extracting out the true or correct heart rate when the algorithm employed pulse priors. The observed PPG graph on the left is hard to interpret as it is easy to see that the color representing the PPG signal is rather weak and does fluctuate significantly. The algorithm overcame this by multiplying the pulse rate probabilities from the FFT with prior distribution. This prevents the Viterbi from locking onto the colored signal on the bottom of the graph which represents a lower harmonic. An advantage of this methodology is that any given prior does not force a pulse rate estimate. If a strong pulse signal appears in the PPG it will still be selected. Accordingly, priors form a good baseline for pulse rate anomaly detection. In this regard, the algorithm computes deviation(s) of the pulse rate distribution from prior (e.g. KL divergence) conditioned on a selected activity state to determine whether individuals have unusual pulse behavior. There is data that shows interesting correlations to heart rate anomaly and one or more disease states in the user. In terms of computing, the pulse rate pathways, the pulse rate transitions were generated by a pulse rate transition probability matrix which is motion dependent. For example, the pulse rate transition probability matrix for idle→walking was very different than the pulse rate transition probability matrix for idle→running. Of course, the priors need to be added to prevent double counting e.e.g during sleep (this requires sleep onset detection). Sophisticated algorithms for PPG denoising and pulse rate extraction, which can be used with the systems and methods disclosed herein include, but are not limited to, sparse signal reconstruction for denoising and deep learning techniques for pulse rate estimation.

FIG. 9. shows the numerical improvement in accuracy for using the pulse rate priors and pathway calculations during walking and running exercise activity states.

Example 2

Figure 10:
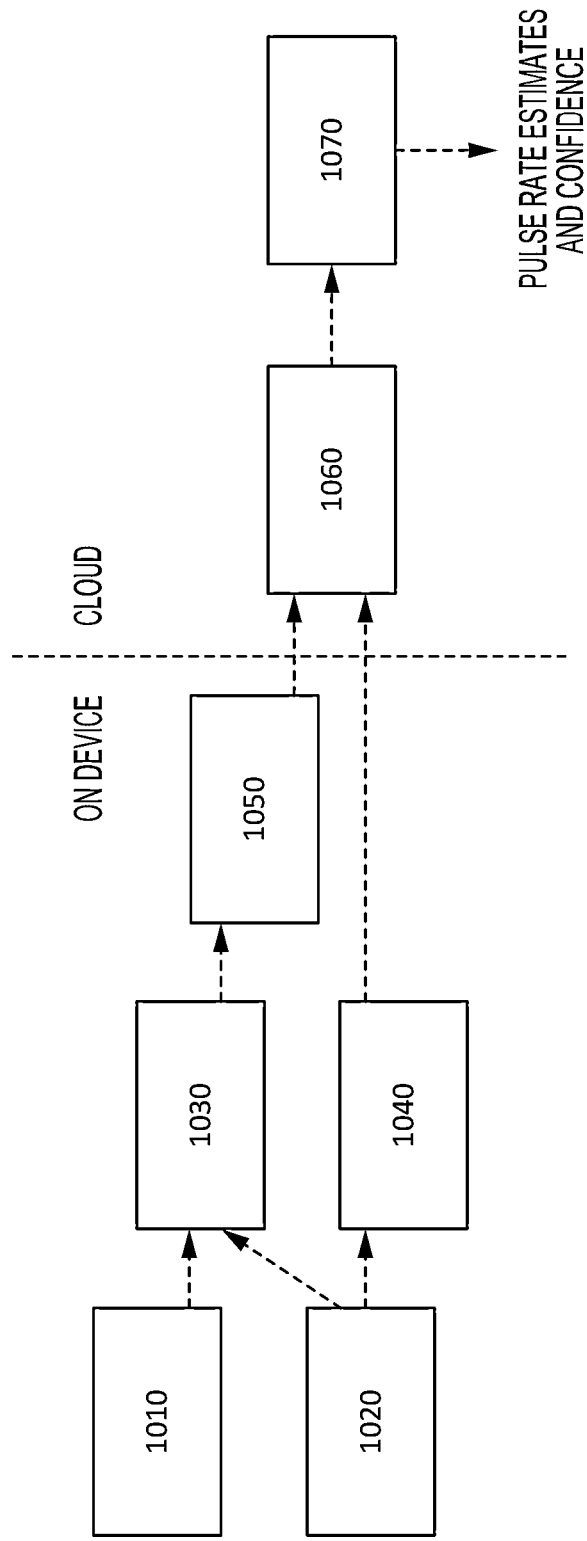
FIG. 10 depicts an example system for determining heart rates.

FIG. 10. shows another potential configuration of the system, wherein on-device functionality includes the activity classification derived from the 3-axis accelerometer, motion-compensation as described in FIG. 4, and Fourier peak detection. A PPG sensor 1010 includes an AFE and ambient light rejection as described elsewhere herein. A 3-axis-accelerometer 1020 provides outputs related to user motion. A motion compensation module 1030 uses the accelerometer outputs to compensate the PPG outputs for user motion. An activity classifier 1040 on the device determines user activity based on the accelerometer outputs. A Fourier peak detection module 1050 on the device determines frequencies and magnitudes of detected peaks in the spectrum of the compensated PPG signal.

The frequencies and magnitudes of the detected peaks, as well as the activity classification, are stored on the device and transferred to the cloud storage. Further processing in the cloud uses a first module 1060 to apply the activity-based prior probabilities to the detected peaks, and reconstructs a sparsified spectrogram from the peak information. The Viterbi path estimator 1070 then identifies the most likely pulse rates at each point in time. Relative to the implementation described in Example 1, this implementation transfers less data to the cloud, enabling data transfer over a wireless link, but is reliant upon a device-resident activity classifier and motion compensation algorithm (which are constrained by the computational capabilities of the device).

What is claimed is:

1. A system comprising:
    a communication interface; and
    a controller that comprises one or more processors, wherein the controller is operably coupled to the communication interface, and wherein the controller is configured to perform operations comprising:
        receiving, from a wearable device using the communication interface, an indication of a motion-compensated cardiovascular signal generated by the wearable device by (i) detecting, using a photoplethysmographic sensor of the wearable device, a photoplethysmographic signal related to cardiovascular activity of a user, (ii) detecting, using a motion sensor of the wearable device, a motion signal related to motion of the user, and (iii) using the motion signal to generate the motion-compensated cardiovascular signal based on the photoplethysmographic signal;
        receiving, from the wearable device using the communication interface, an indication of the motion signal;
        generating a corrected heart rate that has been generated, based on the received indication of the motion-compensated cardiovascular signal and the received indication of the motion signal, by the one or more processors using an algorithm informed by at least one statistical prior for pulse rate transitions between activity states to generate one or more probable pulse paths and using the one or more probable pulse paths to generate the corrected heart rate; and
        transmitting, using the communication interface, an indication of the corrected heart rate to the wearable device.

2. The system of claim 1, wherein receiving the indication of the motion signal from the wearable device comprises receiving an indication of an activity state of the user that has been determined by the wearable device based on the motion signal.

3. The system of claim 1, wherein receiving the indication of the motion-compensated cardiovascular signal from the wearable device comprises receiving an indication of at least one peak associated with a frequency range or frequency value in spectral contents of the motion-compensated cardiovascular signal determined by the wearable device.

4. The system of claim 1, wherein receiving the indication of the motion signal from the wearable device comprises receiving an indication of a first activity state corresponding to a first period of time and an indication of a second activity state corresponding to a second period of time, wherein the motion-compensated cardiovascular signal corresponds to the first and second periods of time, and wherein the operations further comprise:
    determining, by the one or more processors, a first expected heart rate based on the first activity state; and determining, by the one or more processors, a second expected heart rate based on the second activity state;

wherein generating the corrected heart rate comprising determining, by the one or more processors, a time-varying heart rate corresponding to the first and second periods of time, wherein determining a time-varying heart rate comprises (i) determining a first plurality of heart rates corresponding to the first period of time based on the first expected heart rate and the photoplethysmographic signal, and (ii) determining a second plurality of heart rates corresponding to the second period of time based on the second expected heart rate and the photoplethysmographic signal.

5. The system of claim 4, wherein determining time-varying heart rates corresponding to the first and second periods of time comprises using a Viterbi algorithm to determine the time-varying heart rate, wherein the Viterbi algorithm is informed by the first expected heart rate and the second expected heart rate.

6. The system of claim 1, wherein the operations further comprise:
  determining, by the one or more processors based on the indication of the motion signal, a first activity state corresponding to a first period of time;
  determining, by the one or more processors based on the indication of the motion signal, a second activity state corresponding to a second period of time, wherein the motion-compensated cardiovascular signal corresponds to the first and second periods of time;
  determining, by the one or more processors, a first expected heart rate based on the first activity state; and
  determining, by the one or more processors, a second expected heart rate based on the second activity state;
  wherein generating the corrected heart rate comprising determining, by the one or more processors, a time-varying heart rate corresponding to the first and second periods of time, wherein determining a time-varying heart rate comprises (i) determining a first plurality of heart rates corresponding to the first period of time based on the first expected heart rate and the photoplethysmographic signal, and (ii) determining a second plurality of heart rates corresponding to the second period of time based on the second expected heart rate and the photoplethysmographic signal.

7. The system of claim 6, wherein determining time-varying heart rates corresponding to the first and second periods of time comprises using a Viterbi algorithm to determine the time-varying heart rate, wherein the Viterbi algorithm is informed by the first expected heart rate and the second expected heart rate.

8. A non-transitory computer-readable medium having stored thereon instructions executable by at least one processor to perform operations comprising:
  receiving, from a wearable device using a communication interface, an indication of a motion-compensated cardiovascular signal generated by the wearable device by (i) detecting, using a photoplethysmographic sensor of the wearable device, a photoplethysmographic signal related to cardiovascular activity of a user, (ii) detecting, using a motion sensor of the wearable device, a motion signal related to motion of the user, and (iii) using the motion signal to generate the motion-compensated cardiovascular signal based on the photoplethysmographic signal;
  receiving, from the wearable device using the communication interface, an indication of the motion signal;
  generating a corrected heart rate that has been generated, based on the received indication of the motion-compensated cardiovascular signal and the received indication of the motion signal, by the one or more processors using an algorithm informed by at least one statistical prior for pulse rate transitions between activity states to generate one or more probable pulse paths and using the one or more probable pulse paths to generate the corrected heart rate; and
  transmitting, using the communication interface, an indication of the corrected heart rate to the wearable device.

9. The computer-readable medium of claim 8, wherein receiving the indication of the motion signal from the wearable device comprises receiving an indication of an activity state of the user that has been determined by the wearable device based on the motion signal.

10. The computer-readable medium of claim 8, wherein receiving the indication of the motion-compensated cardiovascular signal from the wearable device comprises receiving an indication of at least one peak associated with a frequency range or frequency value in spectral contents of the motion-compensated cardiovascular signal determined by the wearable device.

11. The computer-readable medium of claim 8, wherein receiving the indication of the motion signal from the wearable device comprises receiving an indication of a first activity state corresponding to a first period of time and an indication of a second activity state corresponding to a second period of time, wherein the motion-compensated cardiovascular signal corresponds to the first and second periods of time, and wherein the operations further comprise:
  determining, by the one or more processors, a first expected heart rate based on the first activity state; and
  determining, by the one or more processors, a second expected heart rate based on the second activity state;
  wherein generating the corrected heart rate comprising determining, by the one or more processors, a time-varying heart rate corresponding to the first and second periods of time, wherein determining a time-varying heart rate comprises (i) determining a first plurality of heart rates corresponding to the first period of time based on the first expected heart rate and the photoplethysmographic signal, and (ii) determining a second plurality of heart rates corresponding to the second period of time based on the second expected heart rate and the photoplethysmographic signal.

12. The computer-readable medium of claim 11, wherein determining time-varying heart rates corresponding to the first and second periods of time comprises using a Viterbi algorithm to determine the time-varying heart rate, wherein the Viterbi algorithm is informed by the first expected heart rate and the second expected heart rate.

13. The computer-readable medium of claim 8, wherein the operations further comprise:
  determining, by the one or more processors based on the indication of the motion signal, a first activity state corresponding to a first period of time;
  determining, by the one or more processors based on the indication of the motion signal, a second activity state corresponding to a second period of time, wherein the motion-compensated cardiovascular signal corresponds to the first and second periods of time;
  determining, by the one or more processors, a first expected heart rate based on the first activity state; and
  determining, by the one or more processors, a second expected heart rate based on the second activity state;

wherein generating the corrected heart rate comprising determining, by the one or more processors, a time-varying heart rate corresponding to the first and second periods of time, wherein determining a time-varying heart rate comprises (i) determining a first plurality of heart rates corresponding to the first period of time based on the first expected heart rate and the photoplethysmographic signal, and (ii) determining a second plurality of heart rates corresponding to the second period of time based on the second expected heart rate and the photoplethysmographic signal.

14. The computer-readable medium of claim 13, wherein determining time-varying heart rates corresponding to the first and second periods of time comprises using a Viterbi algorithm to determine the time-varying heart rate, wherein the Viterbi algorithm is informed by the first expected heart rate and the second expected heart rate.

15. The method of claim 8, wherein receiving the indication of the motion signal from the wearable device comprises receiving an indication of a first activity state corresponding to a first period of time and an indication of a second activity state corresponding to a second period of time, wherein the motion-compensated cardiovascular signal corresponds to the first and second periods of time, and wherein the method further comprises:
determining, by the one or more processors, a first expected heart rate based on the first activity state; and
determining, by the one or more processors, a second expected heart rate based on the second activity state;
wherein generating the corrected heart rate comprising determining, by the one or more processors, a time-varying heart rate corresponding to the first and second periods of time, wherein determining a time-varying heart rate comprises (i) determining a first plurality of heart rates corresponding to the first period of time based on the first expected heart rate and the photoplethysmographic signal, and (ii) determining a second plurality of heart rates corresponding to the second period of time based on the second expected heart rate and the photoplethysmographic signal.

16. The method of claim 15, wherein determining time-varying heart rates corresponding to the first and second periods of time comprises using a Viterbi algorithm to determine the time-varying heart rate, wherein the Viterbi algorithm is informed by the first expected heart rate and the second expected heart rate.

17. A method comprising:
receiving, by one or more processors from a wearable device using a communication interface, an indication of a motion-compensated cardiovascular signal generated by the wearable device by (i) detecting, using a photoplethysmographic sensor of the wearable device, a photoplethysmographic signal related to cardiovascular activity of a user, (ii) detecting, using a motion sensor of the wearable device, a motion signal related to motion of the user, and (iii) using the motion signal to generate the motion-compensated cardiovascular signal based on the photoplethysmographic signal;
receiving, by the one or more processors from the wearable device using the communication interface, an indication of the motion signal;
generating a corrected heart rate that has been generated, based on the received indication of the motion-compensated cardiovascular signal and the received indication of the motion signal, by the one or more processors using an algorithm informed by at least one statistical prior for pulse rate transitions between activity states to generate one or more probable pulse paths and using the one or more probable pulse paths to generate the corrected heart rate; and
transmitting, by one or more processors using the communication interface, an indication of the corrected heart rate to the wearable device.

* * * * *